(12) United States Patent
Yamashita et al.

(10) Patent No.: US 6,710,160 B2
(45) Date of Patent: Mar. 23, 2004

(54) POLYAMIC ACID, POLYIMIDE, PROCESS FOR PRODUCING THESE, AND FILM OF THE POLYIMIDE

(75) Inventors: Wataru Yamashita, Fukuoka (JP); Katsuji Watanabe, Fukuoka (JP); Hideaki Oikawa, Fukuoka (JP); Hisato Ito, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/088,481
(22) PCT Filed: Jul. 26, 2001
(86) PCT No.: PCT/JP01/06434
§ 371 (c)(1), (2), (4) Date: Mar. 20, 2002
(87) PCT Pub. No.: WO02/10253
PCT Pub. Date: Feb. 7, 2002

(65) Prior Publication Data
US 2002/0188090 A1 Dec. 12, 2002

(30) Foreign Application Priority Data
Jul. 27, 2000 (JP) ........................................ 2000-226324

(51) Int. Cl.$^7$ .................. C08G 73/10; C08G 69/28; C08L 79/08; B32B 27/00
(52) U.S. Cl. .................. 528/353; 528/125; 528/128; 528/170; 528/172; 528/173; 528/176; 528/179; 528/185; 528/188; 528/220; 528/229; 528/350; 525/420; 525/422; 524/600; 524/602
(58) Field of Search ................ 528/125, 128, 528/170, 172, 173, 176, 188, 220, 229, 350, 353; 525/420, 422; 524/600, 606; 428/473.5

(56) References Cited
U.S. PATENT DOCUMENTS
5,807,961 A * 9/1998 Sawai et al. .................. 528/170

FOREIGN PATENT DOCUMENTS
EP 0 896 014 7/1998
JP 10-7906 1/1998

* cited by examiner
Primary Examiner—P. Hampton Hightower
(74) Attorney, Agent, or Firm—Burns, Doane, Swecker & Mathis, LLP

(57) ABSTRACT

Disclosed are a polyamic acid having repeating units represented by the formula (1):

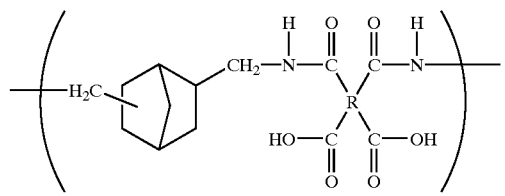

(1)

wherein the norbornane skeleton of

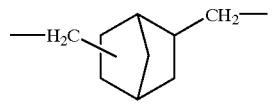

comprises four components of

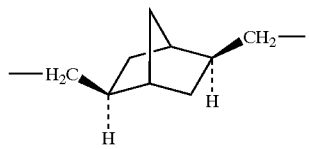

2,5-[diexo]

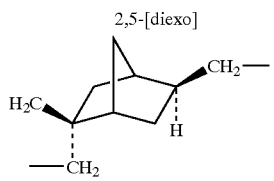

2,5-[exo,endo]

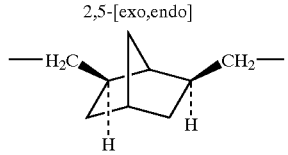

2,6-[diexo]

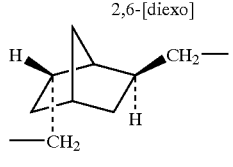

2,6-[exo,endo]

and their contents satisfy the following:
1% ≦ 2,5-[diexo] ≦ 90%,
1% ≦ 2,5-[exo,endo] ≦ 90%,
1% ≦ 2,6-[diexo] ≦ 90%,
1% ≦ 2,6-[exo,endo] ≦ 90%,
provided that (2,5-[diexo])+(2,5-[exo,endo])+(2,6-[diexo])+(2,6-[exo,endo])= 100%, R represents from 4 to 27 carbon atoms, and represents a tetravalent group selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member; and a polyimide which is obtained by imidizing the polyamic acid and which has good properties intrinsic to polyimides, or that is, thermal resistance, mechanical properties, slidability, low water absorption, electric properties and radiation resistance intrinsic thereto. By varying the composition ratio of the starting diamine isomers, various polyimides having controlled thermal resistance, melt flowability, optical properties, chemical resistance and electric properties and capable of forming films of various forms can be obtained.

20 Claims, 2 Drawing Sheets

POLYAMIC ACID, POLYIMIDE, PROCESS FOR PRODUCING THESE, AND FILM OF THE POLYIMIDE

TECHNICAL FIELD

The present invention relates to a polyamic acid, a polyimide and a process for preparing them, for which is used a diamine isomer mixture, as well as to a varnish containing the polyamic acid and a film containing the polyimide. Specifically, the invention relates to a polyimide having excellent thermal resistance, melt flowability, optical properties and chemical resistance and further controlled dielectric properties in addition to excellent physical properties inherent to polyimides, that is, thermal resistance, mechanical properties, slidability, low water absorption, electric properties and radiation resistance, and relates to a polyamic acid being a precursor of the polyimide, to a process for preparing them, and to a varnish or film thereof.

PRIOR ART

Conventionally, polyimides have been widely used as the molding materials, composite materials and electric materials in various fields for excellent mechanical properties and electronic properties in addition to it's excellent thermal resistance.

For example, the polyimide represented by the formula (A):

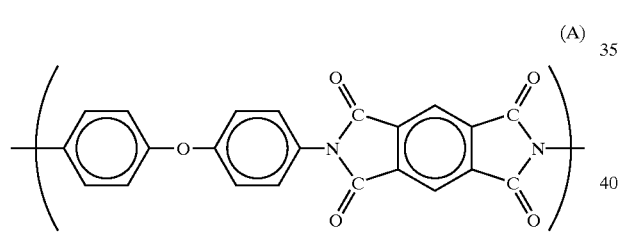

(A)

has been known as a typical polyimide. However, the polyimide is non-thermoplastic, therefore the polyimide has a significant drawback in moldability because of insolubility and infusibility, and there is problem that mass production of its moldings is substantially impossible. One concrete method of processing the polyimide comprises forming it into a mass in a special molding process of powder sinter molding followed by mechanically processing it, by cutting, machining or polishing it to give a shaped article. Films of the polyimide to be used in the field of electronic materials have good thermal resistance and mechanical properties, but their properties are not satisfactory in the field where high-frequency waves are used. In addition, the films are yellowish brown, and therefore cannot be used for optical materials.

The polyimide represented by the formula (B)

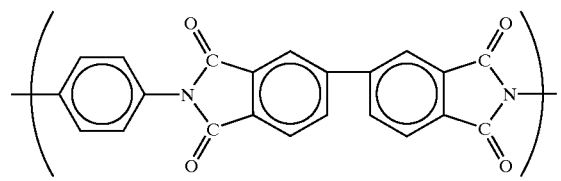

(B)

is also non-thermoplastic, and its use is generally for films, which are mainly used in the field of electronic materials. The polyimide is excellent in thermal resistance and mechanical properties, but its films are yellowish brown and therefore cannot be used for optical materials.

The polyetherimide represented by the formula (C):

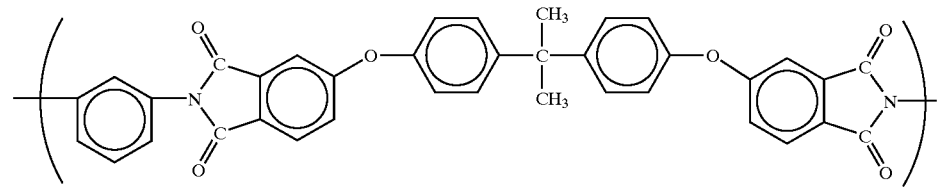

(C)

and the polyimide represented by the formula (D):

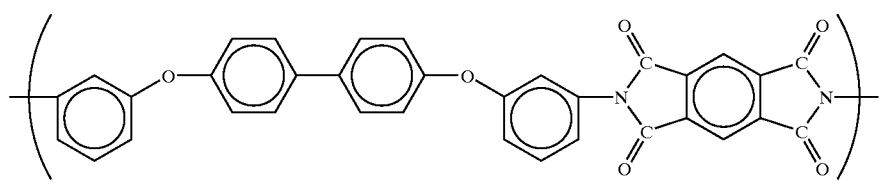

(D)

have been known as a polyimide having an improved moldability and workability.

These polyimides have good properties such as thermal resistance inherent to polyimides, and are generally used for molding materials. However, these are also pale yellow to brown, and are therefore not used for optical materials.

On the other hand, various materials have been developed with the development in optical communication, and materials substitutable for quartz are much studied. As well known, their typical examples are polymethyl methacrylates and polycarbonates. In addition, cyclic polyolefins represented by the formulae (E) and (F) and fluorine-containing polymers represented by the formula (G) have been developed.

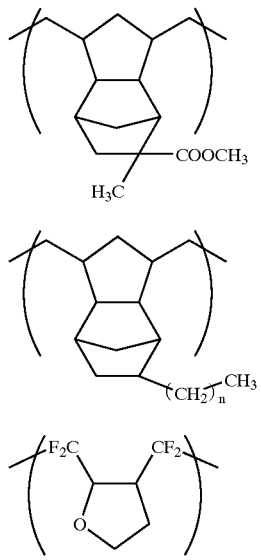

These polymers have excellent optical properties, and their applications are extending for optical fibers, optical wave-guides, optical disc substrates, optical lenses, optical filters, etc. However, the polymers all have a glass transition temperature not higher than about 180° C., and their thermal resistance is unsatisfactory for their use at high temperatures.

Apart from the optical materials mentioned above, electric insulating materials usable in a high frequency region are desired with the development of electronic instruments. According to this, low-dielectric and low-loss materials are being developed. In molecular planning for these, it is said that introducing a fluoro group or a trifluoromethyl group into the main chain skeleton of polymers is indispensable. For example, A. K. St. Clair, et al. of the US National Aeronautics and Space Administration (NASA) has been disclosed various polyimides in Polymeric Materials Science and Engineering, Vol. 59, p. 28 (1988) and EP 0299865; and Yamashita, et al. in U.S. Pat. Nos. 5,354,839 and 5,410,084. For these polyimides, however, extremely expensive starting materials must be used for introducing the essential substituent thereinto, and this is a great obstacle to the practical application of the polyimides.

On the other hand, some methods have been tried for improving the optical properties such as colorless transparency and the electric properties of polyimides without introducing such expensive fluorine thereinto. For example, alicyclic diamine compounds or acid dianhydrides are used for developing polyimides having improved optical properties such as colorless transparency. In the prior art of JP-A 7906/1998 or WO98/29471, used is a mixture of alicyclic diamine compounds, 2,5-diaminomethyl-bicyclo[2.2.1] heptane (hereinafter abbreviated as 2,5-NBDA) and 2,6-diaminomethyl-bicyclo[2.2.1]heptane (hereinafter abbreviated as 2,6-NBDA) to obtain polyimides of good light transmittance (high colorless transparency).

As so mentioned in that WO98/29471, however, these NBDAs used in the prior art are 2,5-substituted and 2,6-substituted isomers and are extremely difficult to separate, and therefore a mixture of the two is directly used as it is. The polyimides formed from these NBDAs are surely better than conventional polyimides in point of their optical properties, but further polyimides having better film properties and better optical properties have been desired in the art.

DISCLOSURE OF THE INVENTION

The object of the present invention is to provide a polyimide having further improved and controlled properties in thermal resistance, melt flowability, optical properties, chemical resistance and electric properties in addition to excellent physical properties inherent to polyimides, that is, thermal resistance, mechanical properties, slidability, low water absorption, electric properties, radiation resistance, and to provide its precursor, a polyamic acid. In addition, the object of the invention is to provide a process for preparing them, and to provide a varnish and a film comprising them, which are important embodiments of their practical use.

The present inventors have assiduously studied so as to attain the above objects.

As a result, the inventors have already found a process for preparing an alicyclic diamine, diaminomethyl-bicyclo [2.2.1]heptane (hereinafter abbreviated as NBDA), in which the composition ratio of the 2,5-substituted isomer and the 2,6-substituted isomer in the diamine isomer mixture can be varied. In addition, the inventors have clarified that the 2,5-substituted isomer and the 2,6-substituted isomer additionally form stereo-isomers, that is, they are in the form of a mixed composition of four structural isomers, (2S,5S)-NBDA, (2S,5R)-NBDA, (2S,6R)-NBDA and (2S,6S)-NBDA. With that, the inventors have further studied the compositions of these NBDA isomers and the properties of the polyamic acids and the polyimides produced from them, and have found out the polyimide of the present invention which naturally has the good properties inherent to polyimides and additionally has further improved and controlled thermal resistance, melt flowability, optical properties, chemical resistance, electric properties and film properties, depending on the composition ratio of the starting isomers used.

Specifically, the present invention relates to the following:

1) A polyamic acid having repeating units represented by the formula (I):

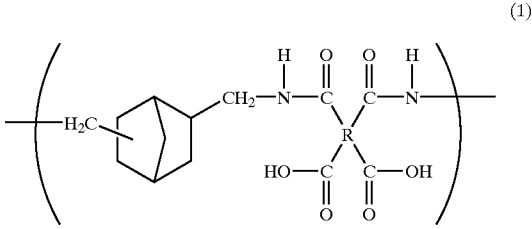

wherein the norbornane skeleton of

—H₂C⟨norbornane⟩CH₂— comprises four components of

—H₂C⟨norbornane⟩CH₂—
     H        H
2,5-[diexo]

H⟨norbornane⟩CH₂—
—CH₂    H
2,5-[exo, endo]

—H₂C⟨norbornane⟩CH₂—
     H        H
2,6-[diexo]

H⟨norbornane⟩CH₂—
—CH₂    H
2,6-[exo, endo]

and their contents satisfy the following:
  $1\% \leq 2,5\text{-[diexo]} \leq 90\%$,
  $1\% \leq 2,5\text{-[exo,endo]} \leq 90\%$,
  $1\% \leq 2,6\text{-[diexo]} \leq 90\%$,
  $1\% \leq 2,6\text{-[exo,endo]} \leq 90\%$,
provided that (2,5-[diexo])+(2,5-[exo,endo])+(2,6-[diexo])+-[exo,endo])=100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

2) A polyamic acid having repeating units represented by the formula (1):

(1)
polyamic acid structure with H₂C-norbornane-CH₂-N(H)-C(=O)-R(-C(=O)-OH)(-C(=O)-OH)-C(=O)-N(H)— wherein the norbornane skeleton of

—H₂C⟨norbornane⟩CH₂— comprises four components of

—H₂C⟨norbornane⟩CH₂—
     H        H
2,5-[diexo]

H⟨norbornane⟩CH₂—
—CH₂    H
2,5-[exo, endo]

—H₂C⟨norbornane⟩CH₂—
     H        H
2,6-[diexo]

H⟨norbornane⟩CH₂—
—CH₂    H
2,6-[exo, endo]

and their contents satisfy the following:
  $10\% \leq 2,5\text{-[diexo]} \leq 40\%$,
  $10\% \leq 2,5\text{-[exo,endo]} \leq 40\%$,
  $10\% \leq 2,6\text{-[diexo]} \leq 40\%$,
  $10\% \leq 2,6\text{-[exo,endo]} \leq 40\%$,
provided that (2,5-[diexo])+(2,5-[exo,endo])+(2,6-[diexo])+(2,6-[exo,endo])=100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

3) A polyamic acid having repeating units represented by the formula (1):

(1)
polyamic acid structure with H₂C-norbornane-CH₂-N(H)-C(=O)-R(-C(=O)-OH)(-C(=O)-OH)-C(=O)-N(H)— wherein the norbornane skeleton of

comprises four components of

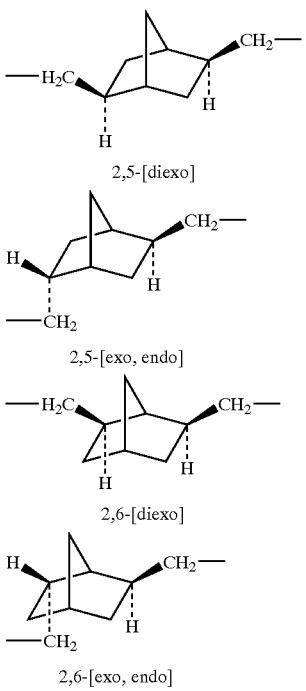

and their contents satisfy the following:

20%≦2,5-[diexo]≦30%,

20%≦2,5-[exo,endo]≦30%,

20%≦2,6-[diexo]≦30%,

20%≦2,6-[exo,endo]≦30%, provided that (2,5-[diexo])+(2,5-[exo,endo])+(2,6-[diexo])+(2,6-[exo,endo])= 100%, R represents a tetravalent group having from 4 to 27 carbon atoms and selected from the group consisting of an aliphatic group, monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

4) A polyimide having repeating units represented by the formula (2):

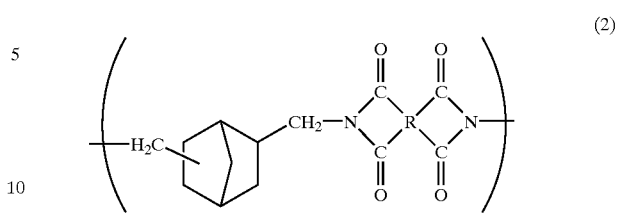

(2)

wherein the norbornane skeleton of

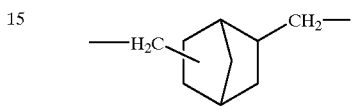

comprises four components of

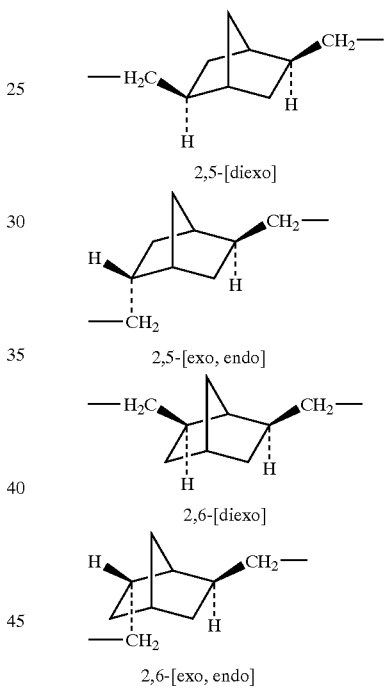

and their contents satisfy the following:

1%≦2,5-[diexo]≦90%,

1%≦2,5-[exo,endo]≦90%,

1%≦2,6-[diexo]≦90%,

1%≦2,6-[exo,endo]≦90%, provided that (2,5-[diexo])+(2,5-[exo,endo])+(2,6-[diexo])+(2,6-[exo,endo])= 100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

5) A polyimide having repeating units represented by the formula (2):

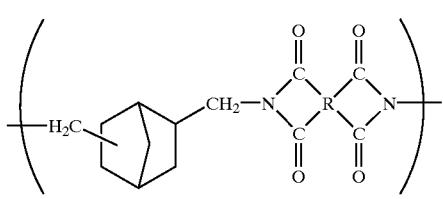

(2)

wherein the norbornane skeleton of

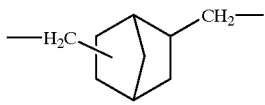

comprises four components of

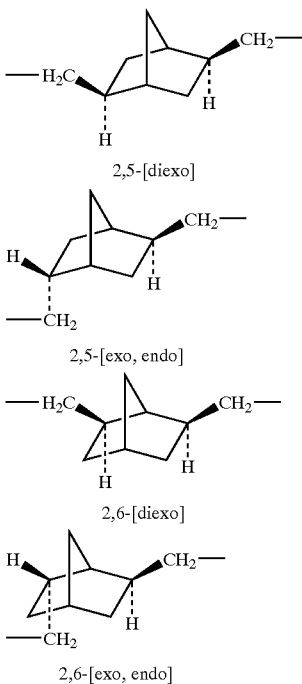

and their contents satisfy the following:
10%≦2,5-[diexo]≦40%,
10%≦2,5-[exo,endo]≦40%,
10%≦2,6-[diexo]≦40%,
10%≦2,6-[exo,endo]≦40%,
provided that (2,5-[diexo])+(2,5-[exo,endo])+(2,6-[diexo])+(2,6-[exo,endo])= 100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

6) A polyimide having repeating units represented by the formula (2):

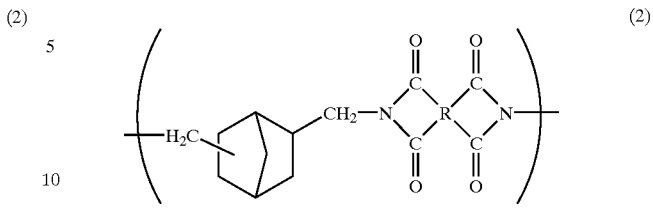

(2)

wherein the norbornane skeleton of

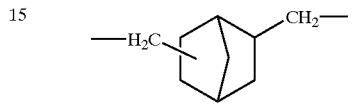

comprises four components of

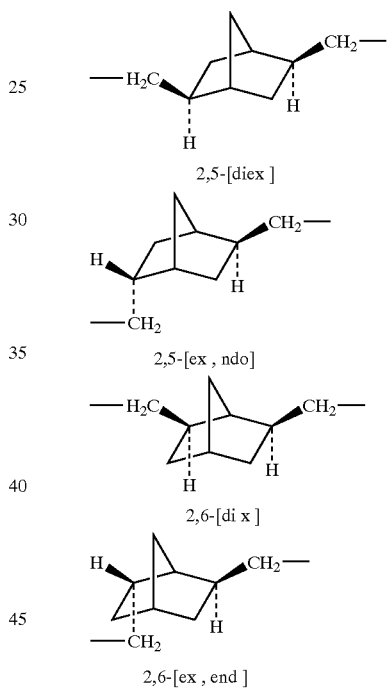

and their contents satisfy the following:
20%≦2,5-[diexo]≦30%,
20%≦2,5-[exo,endo]≦30%,
20%≦2,6-[diexo]≦30%,
20%≦2,6-[exo,endo]≦30%,
provided that (2,5-[diexo])+(2,5-[exo,endo])+(2,6-[diexo])+(2,6-[exo,endo])= 100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

7) A process for preparing a polyamic acid, which comprises reacting a mixture of diaminomethyl-bicyclo[2.2.1]

heptanes, (2S,5S)-diaminomethyl-bicyclo[2.2.1]heptane represented by the formula (3-1):

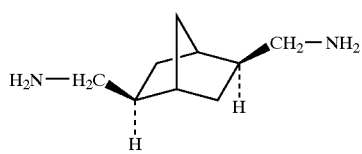

(3-1)

(2S,5R)-diaminomethyl-bicyclo[2.2.1]heptane represented by the formula (3-2):

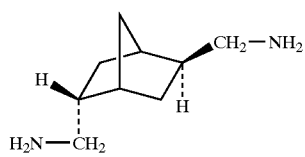

(3-2)

(2S,6R)-diaminomethyl-bicyclo[2.2.1]heptane represented by the formula (3-3):

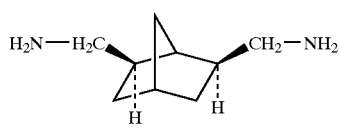

(3-3)

and (2S,6S)-diaminomethyl-bicyclo[2.2.1]heptane represented by the formula (3-4):

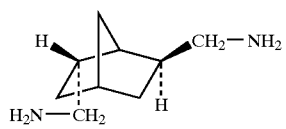

(3-4)

wherein,
  $1\% \leq (2S,5S)$-diaminomethyl-bicyclo[2.2.1]heptane$\leq 90\%$,
  $1\% \leq (2S,5R)$-diaminomethyl-bicyclo[2.2.1]heptane$\leq 90\%$,
  $1\% \leq (2S,6R)$-diaminomethyl-bicyclo[2.2.1]heptane$\leq 90\%$,
  $1\% < (2S,6S)$-diaminomethyl-bicyclo[2.2.1]heptane$\leq 90\%$,
provided that, (2S,5S)isomer+(2S,5R)isomer+(2S,6R)isomer+(2S,6S)isomer= 100%, with a tetracarboxylic dianhydride represented by the formula (4);

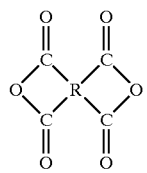

(4)

wherein R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

8) A process for preparing a polyamic acid, which comprises reacting a mixture of diaminomethyl-bicyclo[2.2.1] heptanes, (2S,5S)-diaminomethyl-bicyclo[2.2.1]heptane represented by the formula(3-1):

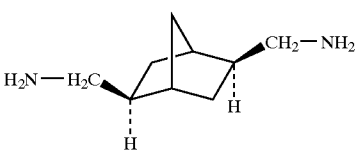

(3-1)

(2S,5R)-diaminomethyl-bicyclo[2.2.1]heptane represented by the formula (3-2):

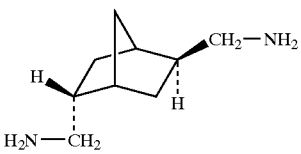

(3-2)

(2S,6R)-diaminomethyl-bicyclo[2.2.1]heptane represented by the formula (3-3):

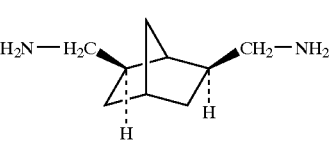

(3-3)

and (2S,6S)-diaminomethyl-bicyclo[2.2.1]heptane represented by the formula (3-4):

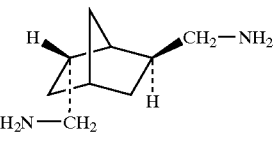

(3-4)

wherein
  $10\% \leq (2S,5S)$-diaminomethyl-bicyclo[2.2.1]heptane$\leq 40\%$,
  $10\% \leq (2S,5R)$-diaminomethyl-bicyclo[2.2.1]heptane$\leq 40\%$,
  $10\% \leq (2S,6R)$-diaminomethyl-bicyclo[2.2.1]heptane$\leq 40\%$,
  $10\% \leq (2S,6S)$-diaminomethyl-bicyclo[2.2.1]heptane$\leq 40\%$,
provided that, (2S,5S)isomer+(2S,5R)isomer+(2S,6R)isomer+(2S,6S)isomer= 100%, with a tetracarboxylic dianhydride represented by the formula (4):

(4)

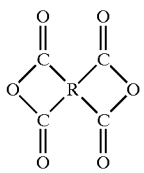

wherein R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

9) A process for preparing a polyamic acid, which comprises reacting a mixture of diaminomethyl-bicyclo[2.2.1]heptanes, (2S,5S)-diaminomethyl-bicyclo[2.2.1]heptane represented by the formula (3-1):

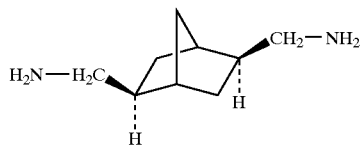
(3-1)

(2S,5R)-diaminomethyl-bicyclo[2.2.1]heptane represented by the formula (3-2):

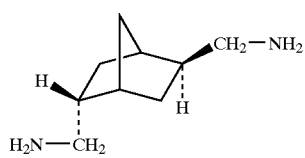
(3-2)

(2S,6R)-diaminomethyl-bicyclo[2.2.1]heptane represented by the formula (3-3):

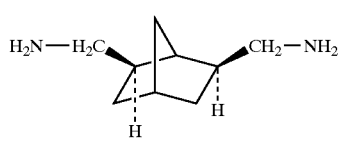
(3-3)

and (2S,6S)-diaminomethyl-bicyclo[2.2.1]heptane represented by the formula (3-4):

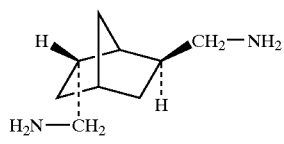
(3-4)

wherein
 20%≦(2S,5S)-diaminomethyl-bicyclo[2.2.1]heptane≦30%,
 20%≦(2S,5R)-diaminomethyl-bicyclo[2.2.1]heptane≦30%,
 20%≦(2S,6R)-diaminomethyl-bicyclo[2.2.1]heptane≦30%,
 20%≦(2S,6S)-diaminomethyl-bicyclo[2.2.1]heptane≦30%,
provided that, (2S,5S)isomer+(2S,5R)isomer+(2S,6R)isomer+(2S,6S)isomer=100%, with a tetracarboxylic dianhydride represented by the formula (4):

(4)

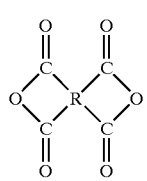

wherein R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member;

10) A process for preparing a polyimide, which comprises thermally or chemically imidizing the polyamic acid obtained in the above 7;

11) A process for preparing a polyimide, which comprises thermally or chemically imidizing the polyamic acid obtained in the above 8;

12) A process for preparing a polyimide, which comprises thermally or chemically imidizing the polyamic acid obtained in the above 9;

13) The polyamic acid of above 1, 2 or 3, of which the inherent viscosity measured in a solvent of N-methyl-2-pyrrolidone having the acid concentration of 0.5 g/dl at 35° C. is in the range of 0.1 to 3.0 dl/g;

14) The polyimide of above 4, 5 or 6, of which the inherent viscosity measured in a mixed solvent of p-chlorophenol/phenol=9/1 (by weight) having the polyimide concentration of 0.5 g/dl at 35° C. is in the range of 0.1 to 3.0 dl/g;

15) A polyamic acid varnish containing the polyamic acid of above 1;

16) A polyamic acid varnish containing the polyamic acid of above 2;

17) A polyamic acid varnish containing the polyamic acid of above 3;

18) A polyimide film containing the polyimide of above 4;

19) An amorphous polyimide film containing the polyimide of above 5;

20) An amorphous polyimide film of improved smoothness, containing the polyimide of above 6.

BEST MODES OF CARRYING OUT THE INVENTION

Figure 1:
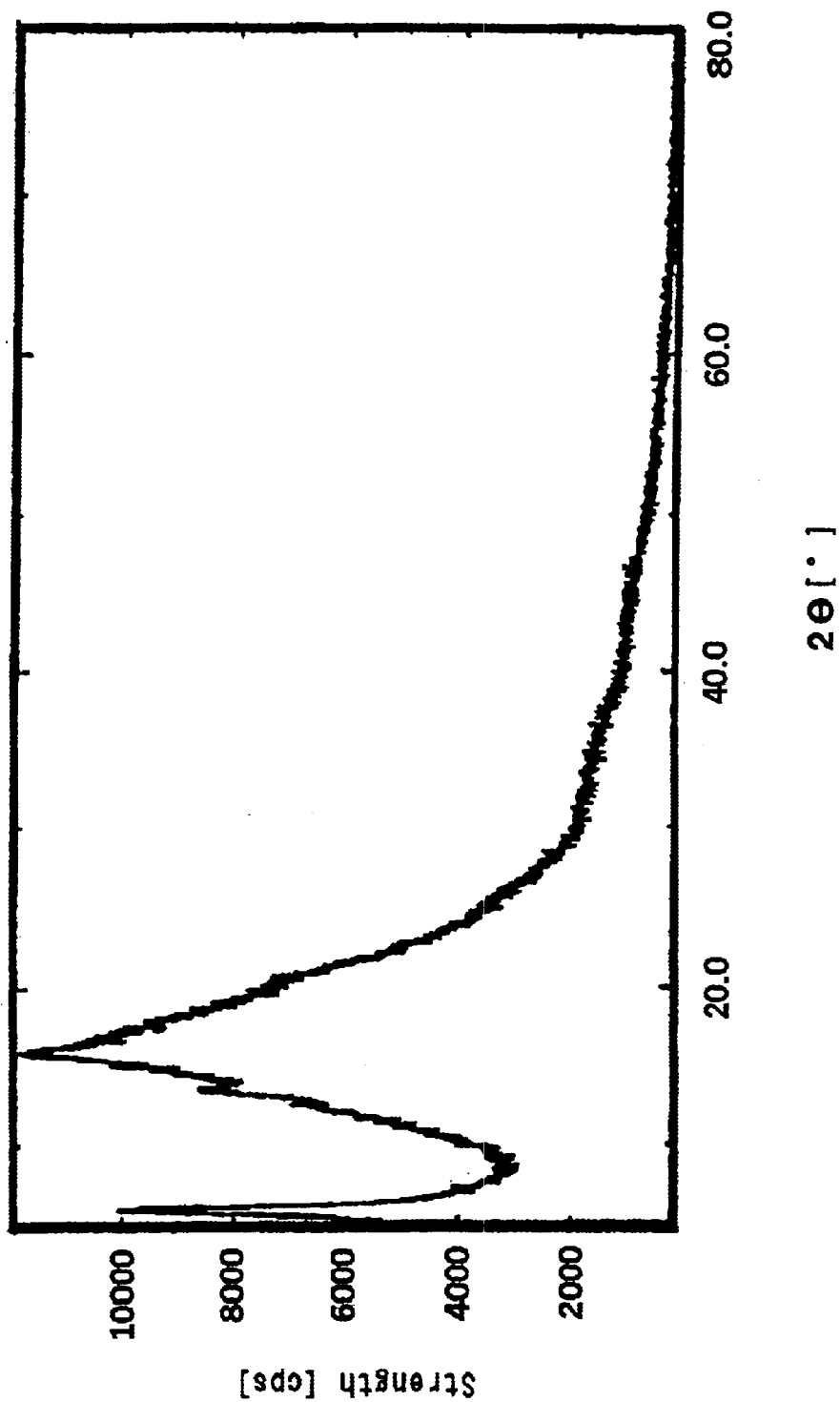
FIG. 1 shows a wide-angle X-ray diffraction pattern of the polyimide film obtained in Example 2.

The essential diamine component in the present invention is diaminomethyl-bicyclo[2.2.1]heptane (NBDA) represented by the formula (3):

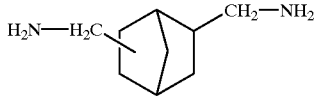
(3)

and includes 2,5- and 2,6-isomers that differ in point of the position of the aminoethyl substituents therein. The NBDA can be obtained by adding hydrogen cyanide to bicyclo [2.2.1]-5-heptene-2-carbonitrile in the presence of a palladium catalyst and triphenyl phosphate to give a dicyano compound followed by catalytically hydrogenating the compound in the presence of a catalyst known for catalytic hydrogenation.

As so mentioned in the prior art disclosure WO98/29471, it is known that the NBDA is extremely difficult to separate into the individual isomer in an ordinary separation method of distillation or the like and therefore is obtained in the form of the isomer mixtures. In Japanese Patent Application No. 363896/1999, the present inventors have disclosed a process for preparing NBDA in which the composition ratio of 2,5-NBDA/2,6-NBDA is varied in any desired manner based on the melting point difference between the isomers.

Through further studies, the present inventors have clarified that NBDA includes the following isomers, including two different stereoisomers of each isomer, and that the composition ratio of those isomers can be varied.

Specifically, the NBDA isomers for the present invention are the following compounds:
(2S,5S)-diaminomethyl-bicyclo[2.2.1]heptane
[(2S,5S)-NBDA] represented by the formula (3-1):

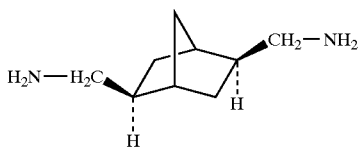
(3-1)

(2S,5R)-diaminomethyl-bicyclo[2.2.1]heptane
[(2S,5R)-NBDA] represented by the formula (3-2):

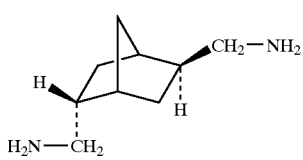
(3-2)

(2S,6R)-diaminomethyl-bicyclo[2.2.1]heptane
[(2S,6R)-NBDA] represented by the formula (3-3):

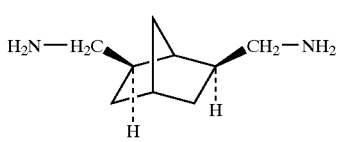
(3-3)

and (2S,6S)-diaminomethyl-bicyclo[2.2.1]heptane
[(2S,6S)-NBDA] represented by the formula (3-4):

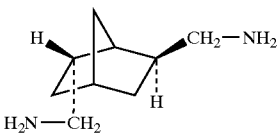
(3-4)

The diamine isomer composition ratio of these four types of NBDA isomers, that is, (2S,5S)-NBDA, (2S,5R)-NBDA, (2S,6R)-NBDA and (2S,6S)-NBDA, can be varied in any desired manner.

In addition, the diamine isomer mixture gives a polyamic acid having the repeating structural units represented by the formula (1), and a polyimide having the repeating structural units represented by the formula (2).

Varying the composition ratio of the starting diamine isomers makes it possible to control the physical properties including thermal resistance, melt flowability, optical properties and chemical resistance of the polyimide to be obtained.

The composition of the NBDA isomers for use in the present invention satisfies the following:

$1\% \leq (2S,5S)\text{-NBDA} \leq 90\%$, $1\% \leq (2S,5R)\text{-NBDA} \leq 90\%$, $1\% \leq (2S,6R)\text{-NBDA} \leq 90\%$, $1\% \leq (2S,6S)\text{-NBDA} \leq 90\%$, provided that

[(2S,5S)-NBDA]+[(2S,5R)-NBDA]+[(2S,6R)-NBDA]+[(2S,6S)-NBDA]=100%;

preferably, $10\% \leq (2S,5S)\text{-NBDA} \leq 40\%$, $10\% \leq (2S,5R)\text{-NBDA} \leq 40\%$, $10\% \leq (2S,6R)\text{-NBDA} \leq 40\%$, $10\% \leq (2S,6S)\text{-NBDA} \leq 40\%$, provided that

[(2S,5S)-NBDA]+[(2S,5R)-NBDA]+[(2S,6R)-NBDA]+[(2S,6S)-NBDA]=100%;

more preferably, $20\% \leq (2S,5S)\text{-NBDA} \leq 30\%$, $20\% \leq (2S,5R)\text{-NBDA} \leq 30\%$, $20\% \leq (2S,6R)\text{-NBDA} \leq 30\%$, $20\% \leq (2S,6S)\text{-NBDA} \leq 30\%$, provided that

[(2S,5S)-NBDA]+[(2S,5R)-NBDA]+[(2S,6R)-NBDA]+[(2S,6S)-NBDA]=100%.

By controlling the ratio of the starting four NBDA isomers in the manner as above, the physical properties of the polyimide obtained can be finally controlled, and it is therefore possible to obtain polyimides having desired physical properties. For example, for obtaining polyimide films of high smoothness, an isomer mixture having an NBDA composition ratio that is in a preferred range is selected, and an isomer mixture having an NBDA composition ratio that is in a more preferred range is selected. As a result, polyimide films of high transparency which do neither curl nor warp and which have excellent properties can be obtained. Curing of films abbreviated herein may be detected according to the following method. A circular film having a diameter of 50 mm and a thickness of 50 μm is dried at 100° C. for 10 minutes, and then left in a thermostat at 23° C. and a humidity of 50% for 24 hours, and the height R (the unit of R is mm) of the swell in the center of the circle is measured, indicating the curvature length. A larger value of the curvature length thus measured means that the film tested curled to a higher degree. Nearer to 0, it means that the film is flatter. In this connection, in general, the value of R is preferably at most 5, more preferably at most 2, even more preferably at most 1.

Isomer mixtures of which the composition oversteps the range defined herein would partially form crystal.

Further, other alicyclic diamines other than NBDA isomer mixtures can be copolymerized in the range of giving no adverse effect on the good properties inherent to polyamides and polyimides.

The amount of the additional diamine is less than 30 mol %, preferably less than 10 mol % per all the diamine component.

The alicyclic diamine compound that may be actually used in the present invention includes, for example,
2,5-diaminomethyl-bicyclo[2.2.2]octane,
2,5-diaminomethyl-7,7-dimethyl-bicyclo[2.2.1]heptane,
2,5-diaminomethyl-7,7-difluoro-bicyclo[2.2.1]heptane,
2,5-diaminomethyl-7,7,8,8-tetrafluoro-bicyclo[2.2.2]-octane,
2,5-diaminomethyl-7,7-bis(hexafluoromethyl)-bicyclo-[2.2.1]heptane,
2,5-diaminomethyl-7-oxa-bicyclo[2.2.1]heptane,
2,5-diaminomethyl-7-thia-bicyclo[2.2.1]heptane,
2,5-diaminomethyl-7-oxo-bicyclo[2.2.1]heptane,
2,5-diaminomethyl-7-aza-bicyclo[2.2.1]heptane,
2,6-diaminomethyl-bicyclo[2.2.2]octane,
2,6-diaminomethyl-7,7-dimethyl-bicyclo[2.2.1]heptane,
2,6-diaminomethyl-7,7-difluoro-bicyclo[2.2.1]heptane,
2,6-diaminomethyl-7,7,8,8-tetrafluoro-bicyclo[2.2.2]-octane,
2,6-diaminomethyl-7,7-bis(hexafluoromethyl)-bicyclo-[2.2.1]heptane,
2,6-diaminomethyl-7-oxy-bicyclo[2.2.1]heptane,
2,6-diaminomethyl-7-thio-bicyclo[2.2.1]heptane,
2,6-diaminomethyl-7-oxo-bicyclo[2.2.1]heptane,
2,6-diaminomethyl-7-imino-bicyclo-2.2.1-heptane,
2,5-diamino-bicyclo[2.2.1]heptane,
2,5-diamino-bicyclo[2,2,2]octane,
2,5-diamino-7,7-dimethyl-bicyclo[2.2.1]heptane,
2,5-diamino-7,7-difluoro-bicyclo[2.2.1]heptane,
2,5-diamino-7,7,8,8-tetrafluoro-bicyclo[2.2.2]octane,
2,5-diamino-7,7-bis(hexafluoromethyl)-bicyclo[2.2.1]-heptane,
2,5-diamino-7-oxa-bicyclo[2.2.1]heptane,
2,5-diamino-7-thia-bicyclo[2.2.1]heptane,
2,5-diamino-7-oxo-bicyclo[2.2.1]heptane,
2,5-diamino-7-aza-bicyclo[2.2.1]heptane,
2,6-diamino-bicyclo[2.2.1]heptane,
2,6-diamino-bicyclo[2.2.2]octane,
2,6-diamino-7,7-dimethyl-bicyclo[2.2.1]heptane,
2,6-diamino-7,7-difluoro-bicyclo[2.2.1]heptane,
2,6-diamino-7,7,8,8-tetrafluoro-bicyclo[2.2.2]octane,
2,6-diamino-7,7-bis(hexafluoromethyl)-bicyclo[2.2.1]-heptane,
2,6-diamino-7-oxy-bicyclo[2.2.1]heptane,
2,6-diamino-7-thio-bicyclo[2.2.1]heptane,
2,6-diamino-7-oxo-bicyclo[2.2.1]heptane,
2,6-diamino-7-imino-bicyclo[[2.2.1]]heptane,
1,2-diaminocyclohexanone,
1,3-diaminocyclohexanone,
1,4-diaminocyclohexanone,
1,2-di(2-aminoethyl)cyclohexane,
1,3-di(2-aminoethyl)cyclohexane,
1,4-di(2-aminoethyl)cyclohexane,
and bis(4-aminocyclohexyl)methane.

These compounds may be used either singly or as a mixture thereof.

Apart from these alicyclic diamine compounds, the acid dianhydride may also be copolymerized with any other aromatic diamines, diaminosiloxanes or aliphatic (and not alicyclic) diamines in the range of giving no adverse effect on the characteristics of the present invention.

The amount of the additional diamine shall be less than 30 mol %, preferably less than 10 mol % per all the diamine component.

The diamine compounds that may be actually used in the present invention, for example, the aromatic diamines include:

A) diamines which have one benzene ring, such as
p-phenylenediamine, m-phenylenediamine and the like,
B) diamines which have two benzene rings, such as
3,3'-diaminodiphenyl ether,
3,4'-diaminodiphenyl ether,
4,4'-diaminodiphenyl ether,
3,3'-diaminodiphenyl sulfide,
3,4'-diaminodiphenyl sulfide,
4,4'-diaminodiphenyl sulfide,
3,3'-diaminodiphenyl sulfone,
3,4'-diaminodiphenyl sulfone,
4,4'-diaminodiphenyl sulfone,
3,3'-diaminobenzophen one,
4,4'-diaminobenzophenone,
3,4'-diaminobenzophenone,
3,3'-diaminodiphenylmethane,
4,4'-diaminodiphenylmethane,
3,4'-diaminodiphenylmethane,
2,2-di(3-aminophenyl)propane,
2,2-di(4-aminophenyl)propane,
2-(3-aminophenyl)-2-(4-aminophenyl)propane,
2,2-di(3-aminophenyl)-1,1,1,3,3,3-hexafluoropropane,
2,2-di(4-aminophenyl)-1,1,1,3,3,3-hexafluoropropane,
2-(3-aminophenyl)-2-(4-aminophenyl)-1,1,1,3,3,3-hexafluoropropane,
1,1-di(3-aminophenyl)-1-phenylethane,
1,1-di(4-aminophenyl)-1-phenylethane,
1-(3-aminophenyl)-1-(4-aminophenyl)-1-phenylethane and the like.
C) diamines which have three benzene rings, such as
1,3-bis(3-aminophenoxy)benzene,
1,3-bis(4-aminophenoxy)benzene,
1,4-bis(3-aminophenoxy)benzene,
1,4-bis(4-aminophenoxy)benzene,
1,3-bis(3-aminobenzoyl)benzene,
1,3-bis(4-aminobenzoyl)benzene,
1,4-bis(3-aminobenzoyl)benzene,
1,4-bis(4-aminobenzoyl)benzene,
1,3-bis(3-amino-α,α-dimethylbenzyl)benzene,
1,3-bis(4-amino-α,α-dimethylbenzyl)benzene,
1,4-bis(3-amino-α,α-dimethylbenzyl)benzene,
1,4-bis(4-amino-α,α-dimethylbenzyl)benzene,
1,3-bis(3-amino-α,α-di-trifluoromethylbenzyl)benzene,
1,3-bis(4-amino-α,α-di-trifluoromethylbenzyl)benzene,
1,4-bis(3-amino-α,α-di-trifluoromethylbenzyl)benzene,
1,4-bis(4-amino-α,α-di-trifluoromethylbenzyl)benzene,
2,6-bis(3-aminophenoxy)benzonitrile,
2,6-bis(3-aminophenoxy)pyridine and the like,
D) diamines which have four benzene rings, such as
4,4'-bis(3-aminophenoxy)biphenyl,
4,4'-bis(4-aminophenoxy)biphenyl,
bis[4-(3-aminophenoxy)phenyl]ketone, bis[4-(4-aminophenoxy)phenyl]ketone,
bis[4-(3-aminophenoxy)phenyl]sulfide,
bis[4-(4-aminophenoxy)phenyl]sulfide,
bis[4-(3-aminophenoxy)phenyl]sulfone,
bis[4-(4-aminophenoxy)phenyl]sulfone,
bis[4-(3-aminophenoxy)phenyl]ether,
bis[4-(4-aminophenoxy)phenyl]ether,
2,2-bis[4-(3-aminophenoxy)phenyl]propane,
2,2-bis[4-(4-aminophenoxy)phenyl]propane,
2,2-bis[3-(3-aminophenoxy)phenyl]-1,1,1,3,3,3-hexafluoropropane,
2,2-bis[4-(4-aminophenoxy)phenyl]-1,1,1,3,3,3-hexafluoropropane and the like,
E) diamines which have five benzene rings, such as
1,3-bis[4-(3-aminophenoxy)benzoyl]benzene,
1,3-bis[4-(4-aminophenoxy)benzoyl]benzene,
1,4-bis[4-(3-aminophenoxy)benzoyl]benzene,
1,4-bis[4-(4-aminophenoxy)benzoyl]benzene,
1,3-bis[4-(3-aminophenoxy)-α,α-dimethylbenzyl]benzene,
1,3-bis[4-(4-aminophenoxy)-α,α-dimethylbenzyl]benzene,
1,4-bis[4-(3-aminophenoxy)-α,α-dimethylbenzyl]benzene,
1,4-bis[4-(4-aminophenoxy)-α,α-dimethylbenzyl]benzene
and the like,
F) diamines which have an aromatic substituent, such as
4,4'-bis[4-(4-aminophenoxy)benzoyl]diphenyl ether,
4,4'-bis[4-(4-amino-α,α-dimethylbenzyl)phenoxy]benzophenone,
4,4'-bis[4-(4-amino-α,α-dimethylbenzyl)phenoxy]diphenyl sulfone,
4,4'-bis[4-(4-aminophenoxy)phenoxy]diphenyl sulfone and the like,
G) diamines which have an aromatic substituent, such as
3,3'-diamino-4,4'-diphenoxybenzophenone,
3,3'-diamino-4,4'-dibiphenoxybenzophenone,
3,3'-diamino-4-phenoxybenzophenone,
3,3'-diamino-4-biphenoxybenzophenone and the like,
H) diamines which have spirobiindane ring such as
6,6'-bis(3-aminophenoxy)-3,3,3',3'-tetramethyl-1,1'-spirobiindane
6,6'-bis(4-aminophenoxy)-3,3,3',3'-tetramethyl-1,1'-spirobiindane and the like.

Diamines derived from the diamines mentioned above by substituting a part or all of the hydrogen atoms on the aromatic ring with a substituent selected from the group consisting of a fluoro group, a methyl group, a methoxy group, a trifluoromethyl group and a trifluoromethoxy group may also be used.

Similarly, diaminosiloxanes and aliphatic diamines may also be used for the copolymerization.

The usable aliphatic diamines are concretely mentioned below.
I) diaminosiloxanes, such as
1,3-bis(3-aminopropyl)tetramethyl disiloxane,
1,3-bis(4-aminobutyl)tetramethyl disiloxane,
α,ω-bis(4-aminopropyl)polydimethyl siloxane,
α,ω-bis(4-aminobutyl)polydimethyl siloxane and the like,
J) ethyleneglycol diamines such as
bis(aminomethyl)ether, bis(2-aminoethyl)ether,
bis(3-aminopropyl)ether,
bis[2-(aminomethoxy)ethyl]ether,
bis[2-(2-aminoethoxy)ethyl]ether,
bis[2-(3-aminopropoxy)ethyl]ether,
1,2-bis(aminomethoxy)ethane,
1,2-bis(2-aminoethoxy)ethane,
1,2-bis[2-(aminomethoxy)ethoxy]ethane,
1,2-bis[2-(2-aminoethoxy)ethoxy]ethane,
ethylene glycol bis(3-aminopropyl)ether,
diethylene glycol bis(3-aminopropyl)ether,
triethylene glycol bis(3-aminopropyl)ether and the like,
K) methylenediamines such as ethylenediamine,
1,3-diaminopropane, 1,4-diaminobutane,
1,5-diaminopentane, 1,6-diaminohexane,
1,7-diaminoheptane, 1,8-diaminooctane,
1,9-diaminononane, 1,10-diaminodecane,
1,11-diaminoundecane, 1,12-diaminododecane and the like.

These diamines may be used either singly or as a mixture thereof.

For the polyamic acid or the polyimide of the present invention, a tetracarboxylic dianhydride represented by the formula (4):

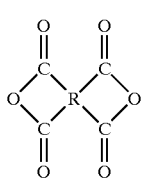

(4)

is used as the essential starting material, and it may be any of aromatic tetracarboxylic dianhydrides or aliphatic tetracarboxylic dianhydrides.

L) The aromatic tetracarboxylic dianhydrides include, for example, pyromellitic dianhydride,
3,3',4,4'-biphenyltetracarboxylic dianhydride,
2,3,3',4'-biphenyltetracarboxylic dianhydride,
3,3',4,4'-benzophenonetetracarboxylic dianhydride,
bis(3,4-dicarboxyphenyl)ether dianhydride,
bis(3,4-dicarboxyphenyl)sulfide dianhydride,
bis(3,4-dicarboxyphenyl)sulfone dianhydride,
bis(3,4-dicarboxyphenyl)methane dianhydride,
2,2-bis(3,4-dicarboxyphenyl)propane dianhydride,
2,2-bis(3,4-dicarboxyphenyl)-1,1,1,3,3,3-hexafluoropropane dianhydride,
1,3-bis(3,4-dicarboxyphenoxy)benzene dianhydride,
1,4-bis(3,4-dicarboxyphenoxy)benzene dianhydride,
4,4'-bis(3,4-dicarbophenoxybiphenyl dianhydride,
2,2-bis[(3,4-dicarboxyphenoxy)phenyl]propane dianhydride,
2,3,6,7-naphthalenetetracarboxylic dianhydride,
1,4,5,8-naphthalenetetracarboxylic dianhydride and the like.
M) Aliphatic tetracarboxylic dianhydrides include, for example,
butane-1,2,3,4-tetracarboxylic dianhydride,
pentane-1,2,4,5-tetracarboxylic dianhydride,
cyclobutanetetracarboxylic dianhydride,
cyclopentane-1,2,3,4-tetracarboxylic dianhydride,
cyclohexane-1,2,4,5-tetracarboxylic dianhydride,
cyclohexa-1-ene-2,3,5,6-tetracarboxylic dianhydride,
3-ethylcyclohexa-1-ene-3-(1,2), 5,6-tetracarboxylic dianhydride,
1-methyl-3-ethylcyclohexane-3-(1,2), 5,6-tetracarboxylic dianhydride,
1-methyl-3-ethylcyclohexa-1-ene-3-(1,2), 5,6-tetracarboxylic dianhydride,
1-ehtylcyclohexane-1-(1,2)3,4-tetracarboxylic dianhydride,
1-propylcyclohexane-1-(2,3), 3,4-tetracarboxylic dianhydride,
1,3-dipropylcyclohexane-1-(2,3), 3-(2,3)-tetracarboxylic dianhydride,
dicyclohexyl-3,4,3',4'-tetracaroxylic dianhydride,
bicyclo[2.2.1]heptane-2,3,5,6-tetracarboxylic dianhydride,
bicyclo[2.2.2]octane-2,3,5,6-tetracarboxylic dianhydride,
bicyclo[2.2.2]octo-7-ene-2,3,5,6-tetracarboxylic dianhydride and the like. These tetracarboxylic dianhydrides may be used either singly or as a mixture thereof at the same time.

N) The polyamic acid and the polyimide of the present invention are represented by the above-mentioned formulae (1) and (2), respectively, in which the molecular terminals may be blocked or not. In case where the molecular terminals are blocked, it is desirable that they are blocked with a group not reactive with amines or dicarboxylic anhydrides, as so known in the art.

Concretely, it is desirable that the molecular terminals of the polymers having repeating structural units represented by the formula (1) or (2) are blocked with an aromatic dicarboxylic anhydride represented by the formula (5):

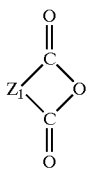
(5)

wherein $Z_1$ represents a divalent group having from 6 to 15 carbon atoms and selected from the group consisting of a monocyclic aromatic group, a condensed polycyclic aromatic group, and a non-condensed polycyclic aromatic group which is composed of aromatic groups mutually bonded to each other either directly or via a crosslinking member, or an aromatic monoamine represented by the formula (6):

$$Z_2-NH_2 \quad (6)$$

wherein $Z_2$ represents a monovalent group having from 6 to 15 carbon atoms and selected from the group consisting of a monocyclic aromatic group, a condensed polycyclic aromatic group, and a non-condensed polycyclic aromatic group, which is composed of aromatic groups mutually bonded to each other either directly or via a crosslinking member.

The dicarboxylic anhydride represented by the formula (5) to be used for obtaining the polyamic acid and the polyimide of the invention includes phthalic anhydride, 4-phenylphthalic anhydride, 4-phenoxyphthalic anhydride, 4-phenysulfinylphthalic anhydride, 4-phenylsulfonylphthalic acid anhydride, 4-phenylcarbonylphthalic anhydride, 4-(2-phenylisopropyl)phthalic anhydride, 4-(1,1,1,3,3,3-hexafluoro-2-phenylisopropyl)phthalic anhydride, 1,8-naphtalenedicarboxylic anhydride and the like. These dicarboxylic anhydrides are used either singly or as a mixture thereof.

The amount of the dicarboxylic anhydride to be used is in the range of from 0.001 to 1.0 mol per mol of all the diamine compound, Preferably in the range of 0.01 to 0.5 mols.

O) The aromatic monoamine represented by the formula (6) used for obtaining the polyamic acid and the polyimide includes aniline, toluidines, xylidines, chloroanilines, bromoanilines, nitroanilines, aminophenols, anisidines, phenetidines, aminobenzaldehydes, aminobenzonitriles, aminobiphenyls, aminophenylphenyl ethers, aminobenzophenones, aminophenylphenyl sulfides, aminophenylphenyl sulfones, naphthylamines, aminonaphthols, aminoanthracenes and the like.

These aromatic monoamines may be substituted with a substituent not reactive with amines and dicarboxylic anhydrides. These aromatic monoamines may be used either singly or as a mixture thereof.

The amount of the aromatic monoamine used is in the range of from 0.001 to 1.0 mol per mol of all the tetracarboxylic dianhydride, preferably, in the range of from 0.01 to 0.5 mols.

In preparing polyamic acids or polyimides, the blend ratio of the tetracarboxylic dianhydride to the diamine compound is generally controlled so as to control the molecular weight of the polyamic acids or polyimides to be prepared. In the process of the present invention, the molar ratio of all the diamine compound to all the dianhydride must be in the range of from 0.9 to 1.1. The mode of blocking the molecular terminals of the polyamic acid or the polyimide of the present invention is grouped into the following two.

In one case, an excess of the diamine compound is used and the terminals are blocked with an aromatic dicarboxylic anhydride. In this case, the amount of the tetracarboxylic dianhydride is in the range of from 0.9 to less than 1.0 mol and that of the aromatic dicarboxylic anhydride is in the range of from 0.001 to 1.0 mol, per mol of the diamine compound.

In the other case, an excess of the dianhydride is used and the terminals are blocked with an aromatic monoamine. In this case, the amount of the diamine compound is in the range of from 0.9 to less than 1.0 mol and that of the aromatic monoamine is in the range of from 0.001 to 1.0 mol, per mol of the tetracarboxylic dianhydride.

The polymers controlled the molecular weight and blocked at the molecular terminals in the manner as above have good melt flowability and are easy to mold in melt.

In case where the molar ratio of all the diamine compound to the dianhydride is defined in the range of 0.9 to 1.1, the molecular weight of the polyamic acid and the polyimide to be obtained will be as follows: specifically, the inherent viscosity of the polyamic acid, measured in a solvent of N-methyl-2-pyrrolidone having the acid concentration of 0.5 g/dl at 35° C., is in the range of 0.1 to 3.0 dl/g; and the inherent viscosity of the polyimide, measured in a mixed solvent of p-chlorophenyl/phenol=9/1 (by weight) having the polyimide concentration of 0.5 g/dl at 35° C., is in the range of 0.1 to 3.0 dl/g.

In case where the polyimide of the present invention is a copolymer, sequential control and regularity of two or more repeating units that constitute the copolymer may be limited or not; and the copolymer may be in any form of random, alternate or block copolymers. Accordingly, when the polymers are composed of three or more different diamine and tetracarboxylic dianhydride, the order of adding the raw materials to a reactor is not specifically limited, and may be added thereto all at a time or successively in divided portions. When two or more diamine isomer mixtures that differ in point of the composition ratio of the four NBDA isomers constituting them are used, the diamine composition in the polymer obtained may be locally unbalanced even though the comonomers are copolymerized in a mode of random copolymerization.

In polymerizing them, the method of adding the starting monomers to a polymerization reactor is not specifically limited. For example, employable methods are as the following:

i) A diamine compound is first reacted with a tetracarboxylic dianhydride, and then with a dicarboxylic anhydride or a monoamine added thereto;

ii) A diamine compound is reacted with a dicarboxylic anhydride added thereto, and then further reacted with a tetracarboxylic dianhydride added thereto;

iii) A tetracarboxylic dianhydride is reacted with a monoamine added thereto, and then further reacted with a diamine compound added thereto;

iv) A tetracarboxylic dianhydride is reacted with a diamine compound along with a dicarboxylic acid or a monoamine added thereto, all at a time.

Any of these methods of addition may be employed herein.

The reaction is generally carried out in a solvent.

The solvent includes;

a) phenol based solvent such as phenol, o-chlorophenol, m-chlorophenol, p-chlorophenol, o-cresol, m-cresol, p-cresol, 2,3-xylenol, 2,4-xylenol, 2,5-xylenol, 2,6-xylenol, 3,4-xylenol, 3,5-xylenol and the like, b) aprotic amide based solvent such as N,N-dimethylformamide, N,N-dimethylacetamide, N,N-diethylacetamide, N-methyl-2-pyrrolidone, 1,3-dimethyl-2-imidazolidinone, N-methylcaprolactam, hexamethylphosphoric triamide and the like.

c) ether based solvent such as 1,2-dimethoxyethane, bis(2-methoxyethyl)ether, 1,2-bis(2-methoxyethoxy)ethane, tetrahydrofuran, bis[2-(2-methoxyethoxy)ethyl]ether, 1,4-dioxane and the like, d) amine based solvent such as Pyridine, quinoline, isoquinoline, α-picoline, β-picoline, γ-picoline, isophorone, piperidine, 2,4-rutidine, 2,6-lutidine, triethylamine, triethylamine, tripropylamine, tributylamine and the like, and e) other solvent such as dimethylsulfoxide, dimethylsulfone, diphenylether, sulfolane, diphenylsulfone, tetramethylurea, anisole and the like.

These solvents may be used either singly or as a mixture thereof.

As the case may be, the solvents mentioned in the following f), g), h) and i) may also be used either singly or as combined. In case where the solvents are combined for use herein, they are not always required to be specifically so selected that they can mutually dissolve in a desired ratio. If not miscible with each other, the solvents combined may form an inhomogeneous mixture.

The concentration of the reaction that is carried out in these solvents (this is hereinafter abbreviated as a polymerization concentration) is not specifically limited at all.

In the present invention, the polymerization concentration in a solvent is defined as the ratio in terms of percentage of the overall weight of all the diamine and all the tetracarboxylic dianhydride used to the sum total of the overall weight of all the solvent used and the overall weight of all the diamine and all the tetracarboxylic dianhydride used. Preferably, the polymerization concentration is in the range of 5 to 40%, more preferably in the range of 10 to 30%.

The reaction is preferably carried out in a solvent, for which, for example, the following processes are employable.

i) A diamine and a tetracarboxylic dianhydride are reacted in melt at a temperature not lower than the melting point of the reactants (in general, this is referred to as melt polymerization or flux polymerization);

ii) A diamine and a tetracarboxylic dianhydride are vaporized, for example, by heating them under reduced pressure, and then reacted in a vapor phase (in general, this is abbreviated as sputtering or vacuum vapor deposition);

iii) A diamine and a tetracarboxylic dianhydride are activated by applying external energy of ultrasonic waves or plasmas thereto, and then reacted;

iv) A polyamic acid or polyimide oligomer is prepared, for example, in the above-mentioned solution method, and this is polymerized in a solid phase in the absence of a solvent;

v) A diamine and a tetracarboxylic acid are reacted to form a salt monomer (nylon salt), the monomer is then isolated and polymerized in a solid phase in the absence of a solvent.

In the reaction to give the polyamic acid having repeating units represented by the formula (I) or the polyamic acid having repeating units represented by the formula (I) and blocked at the molecular terminals, the aprotic amide based solvents b) and the ether based solvents c) mentioned above are especially preferred. The reaction temperature, the reaction time and the reaction pressure are not specifically limited, and any known conditions may apply to these. The reaction temperature preferably is in the range of about −10 to about 100° C., more preferably in the range of around the freezing temperature to 50° C., and most preferably in practice, it is room temperature.

The reaction time varies depending on the type of the monomers used, the type of the solvent used and the reaction temperature, but preferably is in the range of 1 and 48 hours, more preferably in the range of 2 or 3 hours to over ten hours, and most preferably in practice, it is in the range of 4 to 10 hours. For the reaction pressure, normal pressure will be enough.

The polyimide having repeating units represented by the formula (2) and the polyimide having repeating units represented by the formula (2) and blocked at the molecular terminals can be obtained through known dehydrating imidation of the polyamic acid obtained in the method mentioned above. The method of dehydrating imidation is grouped into chemical imidation and thermal imidation. Including the combination of the two, any and every dehydrating imidation may apply to the preparation of the polyimide.

The process of chemical imidation comprises reacting the polyamic acid obtained in the process mentioned above with a dehydrating agent having the ability to hydrolyze the acid to thereby chemically dehydrate the acid. The dehydrating agent usable in the process includes aliphatic carboxylic anhydrides such as typically acetic anhydride and trifluoroacetic anhydride; phosphoric acid derivatives such as typically polyphosphoric acid and phosphorus pentoxide; mixed anhydrides of those acids; and acid chlorides such as typically methanesulfonic acid chloride, phosphorus pentachloride and thionyl chloride. Two or more of these dehydrating agents may be used either singly or as combined. The amount of the dehydrating agent to be used is in the range of 2 to 10 mols per mol of the overall amount of all the diamine used. Preferably, it is in the range of 2.1 to 4 mols.

In the process of chemical imidation, a base catalyst may be present in the reaction system. For the base catalyst, usable are the amine solvents e) mentioned hereinabove.

Apart from these, also usable are organic bases such as imidazole, N,N-dimethylaniline, N,N-diethylaniline; and inorganic bases such as typically potassium hydroxide, sodium hydroxide, potassium carbonate, sodium carbonate, potassium hydrogencarbonate, sodium hydrogencarbonate. The amount of the catalyst to be used is in the range of 0.001 to 0.50 mols per mol of the overall amount of all the diamine used. Preferably, it is in the range of 0.05 to 0.2 mols.

The reaction temperature, the reaction time and the reaction pressure for the chemical imidation are not specifically limited, and any known conditions may apply thereto. Concretely, the reaction temperature preferably is in the range −10 to 120° C., more preferably in the range of around room temperature to 70° C., and most preferably in practice, it is room temperature. The reaction time varies depending on the type of the solvent used and on the other reaction conditions, but preferably is in the range of 1 to 24 hours, more preferably in the range of 2 to 10 hours. For the reaction pressure, normal pressure will be enough. The atmosphere for the reaction is not specifically limited, and may be any of air, nitrogen, helium, neon or argon. Preferably, however, an inert gas, nitrogen or argon is selected for the reaction atmosphere.

The thermal imidation may be carried out as follows:

i) The polyamic acid obtained in the process as above is heated to thermally dehydrate it;

ii) Not preparing the polyamic acid, the polymerization to give the polyamic acid and the dehydrating imidation to give the polyimide are carried out at the same time. For this, the monomers and the dicarboxylic anhydrides to be used are dissolved or suspended in a solvent, and are directly heated for thermal dehydration.

In the process i), the polyamic acid may be dissolved in solution or dispersed in suspension, or a powdery or granular solid of the polyamic acid may be isolated from the solution or suspension. The polymer solution or suspension, or the solid polymer may be heated for thermal dehydration. In case where the polymer solution or suspension is heated, the solvent may be removed through evaporation or may be refluxed during the dehydrating imidation. The former is most favorable for film formation, while the latter is suitable for dehydrating imidation in a reactor. Phenol solvents such as those of the above a) are especially favorable for the process ii).

Like the chemical imidation, the thermal imidation may be carried out in the presence of a base catalyst. The base catalyst and its amount to be used in the thermal imidation, are abbreviated those mentioned hereinabove for the chemical imidation.

To remove water formed through the dehydrating imidation, an additional solvent maybe added in the reaction system. The solvent includes f) benzene, toluene, o-xylene, m-xylene, p-xylene, chlorobenzene, o-dichlorobenzene, m-dichlorobenzene, p-dichlorobenzene, bromobenzene, o-dibromobenzene, m-dibromobenzene, p-dibromobenzene, o-chlorotoluene, m-chlorotoluene, p-chlorotoluene, o-bromotoluene, m-bromotoluene, p-bromotoluene and the like.

These solvents may be used either singly or as a mixture thereof. As the case may be one or more solvents selected from those of the above a) to e) and g) to i) may also be used either singly or as a mixture. In case where the solvents use as a mixture, they are not always required to be specifically selected from the solvents that they can mutually dissolve in a desired ratio. If not miscible with each other, the solvents combined may form an inhomogeneous mixture. The amount of the dehydrating agent used herein is not specifically limited at all.

The reaction temperature, the reaction time and the reaction pressure for the thermal imidation are not specifically limited, and any known conditions may apply thereto. Concretely, the reaction temperature may is in the range of 80 to 400° C., preferably in the range of 100 to 300° C., and most preferably in practice, it is in the range of 150 to 250° C. The reaction time varies depending on the type of the solvent used and on the other reaction conditions, but preferably is in the range of 0.5 to 24 hours, more preferably in the range of 2 to 10 hours. For the reaction pressure, normal pressure will be enough. The atmosphere for the reaction is not specifically limited, and may be any of air, nitrogen, helium, neon or argon. Preferably, however, an inert gas, nitrogen or argon is selected for the reaction atmosphere.

The chemical imidation and the thermal imidation may be combined, for example, as follows:

i) The chemical imidation is carried out under heat;
ii) The thermal imidation is carried out in the presence of a dehydrating agent such as that used for the chemical imidation.

The solution or suspension of the polyimide of the present invention prepared in the processes as above has an important meaning in shaping the polyimide into articles in a mode of solution processing or melt molding. To prepare the polyimide solution or suspension, used is a solvent not chemically reacting with the polyimide.

For this, usable solvent are the solvents a) to e) and f) mentioned above, as well as the following:

g) acetone, methylethyl ketone, methyl-isobutyl ketone, methanol, ethanol, propanol, iso-propanol, butanol, iso-butanol, pentane, hexane, heptane, cyclohexane, dichloromethane, chloroform, carbon tetrachloride, fluorobenzene, methylacetate, ethylacetate, butylacetate, methylformate, ethylformate and the like.

h) water and aqueous solutions containing any of the amine solvents e) mentioned above, imidazole, N,N-dimethylaniline, N,N-diethylaniline, potassium hydroxide, sodium hydroxide, potassium carbonate, sodium carbonate, potassium hydrogencarbonate and sodium hydrogencarbonate;

i) silicone oil, machine oil, operating oil, kerosene, gasoline, jet fuel.

These solvents maybe used either singly or as a mixture thereof. In case where the solvents are combined for use herein, they are not always required to be specifically selected from the solvents that they can mutually dissolve in a desired ratio. Solvents not miscible with each other may be combined.

The solution or suspension containing the polyimide of the present invention may be prepared in any desired manner, for which the method is not specifically limited.

In other words, the conditions for preparing it, including the temperature, the time, the polymer concentration and the pressure are not specifically limited, and, in addition, any known methods are employable for stirring, mixing and dispersing the polymer, and also for preparing the polymer solution or suspension. Concretely, the polyimide solution or suspension may be prepared as follows:

i) The solution or suspension obtained through the reaction to give the polyimide of the present invention is directly used as it is;
ii) The polyimide of the present invention is once isolated to obtain its powder, granules or block, and it is again dissolved or suspended in a solvent such as that mentioned above.

In preparing the polymer solution or suspension, a dispersion promoter and an emulsifier may be added thereto.

Two or more different solutions or suspensions of the polyimide of the present invention prepared in the manner as above may be mixed. Concretely for this, the polyamic acid solutions are mixed after the polymerization to give them; or the polyimide powders or their solutions, or the polyimide solution and the polyimide powder are mixed in a known manner. The polymer solutions and powders to be mixed are not specifically limited in point of the type of the repeating units constituting the respective polymers, and the molecular weight and the molecular weight distribution of the respective polymers, and in point of the polymer concentration and the blend ratio of the polymers for the polymer solutions. The conditions and the methods for mixing them are not also specifically limited at all.

The polyimide of the present invention can be molded in melt. The molding method applicable to it includes extrusion, injection molding, compression molding, sinter molding, blow molding, vacuum forming, rotary molding, powder molding, reactive injection molding, lamination and casting.

In the range of not impairing the object of the invention, the polyimide of the present invention may be blended or alloyed with any other thermoplastic resin such as polyethylene, polypropylene, polyvinyl chloride, polyvinylidene chloride, polybutadiene, polystyrene, polyvinyl acetate, ABS resin, polybutylene terephthalate, polyethylene terephthalate, polyphenylene oxide, polycarbonate, PTFE, celluloid, polyarylate, polyether nitrile, polyamide, polysulfone, polyether sulfone, polyether ketone, polyphenyl sulfide, polyamidimide, polyether imide, modified polyphenylene oxide, and polyimide except that of the invention, and any other thermosetting resin such as thermosetting polybutadiene, formaldehyde resin, amino resin, polyurethane, silicone resin, SBR, NBR, unsaturated polyester, epoxy resin, polycyanate, phenolic resin, and polybismaleimide resin.

Depending on the object of the invention, one or more of such additional resins may be combined with the polyimide in any desired ratio. The method for it is not specifically limited and may be carried out in any known manner.

Also, in the range of not impairing the object of the present invention, the polyimide of the invention may be mixed with various fillers or additives. Their examples are abrasion resistance improver such as graphite, carborundum, silica powder, molybdenum disulfide, fluororesin; flame retardancy promoter such as antimony trioxide, magnesium carbonate, calcium carbonate; electric characteristic improver such as clay, mica; tracking resistance improver such as asbestos, silica, graphite; acid resistance improver such as barium sulfate, silica, calcium metasilicate; thermal conductivity improver such as iron powder, zinc poser, aluminium powder, copper powder; as well as glass beads, glass balloons, talc, diatomaceous earth, alumina, white sand balloons, alumina hydrate, metal oxides, colorants and pigments. The method of mixing the polymer with these is not specifically defined and may be carried out in any known manner.

EXAMPLES

The invention is explained in more detail with reference to the following Examples, which, however, are not intended to restrict the scope of the invention.

The methods of the tests that are common to Examples are mentioned below.

1) Inherent Viscosity of Polyimide:

0.50 g of a sample to be measured is dissolved under heat in 100 ml of a mixed solvent of p-chlorophenol and phenol (90/10 by weight). After cooled to 35° C., the solution is measured.

2) Inherent Viscosity of Polyamic Acid:

A polyamic acid to be measured is dissolved in N-methyl-2-pyrrolidone to have a solid concentration of 0.5 g/dl. After cooled to 35° C., the solution is measured.

3) Melt Flow Point:

Measured in the die diameter of 1.0 mm, the die length of 10 mm; and the load of 100 kgf/cm$^2$ by using a vertical flow tester, Shimadzu Seisakusho's CFT500A Model at the preheating time of 5 min. and the heating rate of 5° C./min.

4) Melt Viscosity:

Measured in the die diameter of 1.0 mm, the die length of 10 mm and the load of 100 kgf/cm$^2$ by using a vertical flow tester, Shimadzu Seisakusho's CFT500A Model at the preheating time of 5 min.

5) 5% Weight Loss Temperature (Td5):

Measured by DTA-TG in the air at a heating rate of 10° C./min with a Shimadzu DTA-TG, DT-40M Model (Shimazu Seisakusyo).

6) Glass Transition Temperature (Tg):

Measured by DSC in nitrogen at a heating rate of 16° C./min. with a Shimadzu Seisakusho's DSC, DT-41M Model.

7) Tensile Strength (TS), Elongation at Break (EL), and Tensile Modulus (TM):

Measured in accordance with ASTM-D-822 by using Shimadzu Seisakusho's EZ-TEST-100N.

8) Dielectric Constant:

Measured in the electrode of 38 mm in length and the frequency of 1 MHz by using a Hewlett-Packard's LCR meter, HP-4284A Model (with bridge) in accordance with JIS-K6911.

9) Resistivity (Volume, Surface):

Measured in the electrode of 38 mm in length and the voltage of 500 V by using a Hewlett-Packard's high-voltage meter, HP-4339A/16008B.

10) Yellowness Index (YI):

Measured the transmitted light by using a Suga Test Instruments' color computer, SM-5 Model.

11) Birefringence:

Measured at a wavelength of 633 nm and 1300 nm. by using a METRICON's prism coupler, 2010 Model.

12) Refractive Index:

Measured in the same manner as in the above 11).

13) E-Type Mechanical Viscosity:

Measured at 25° C. using a Tokyo Keiki's E-type mechanical viscometer.

14) Curl Height R of Film:

A circular film having a diameter of 50 mm and a thickness of 50 µm is dried at 100° C. for 10 minutes, and then left in a thermostat at 23° C. and a humidity of 50% for 24 hours, and the height R (the unit of R is mm) of the swell in the center of the circle is measured, indicating the curvature length. A larger value of the curvature length thus measured means that the film tested curled to a higher degree. Nearer to 0, it means that the film is flatter.

The abbreviations of the starting materials and the solvents that are common to Examples and Comparative Examples and to their Tables are mentioned below.

i) Essential Diamine:

NBDA: mixture of starting compounds,
    (2S,5S)-diaminomethyl-bicyclo[2.2.1]heptane,
    (2S,5R)-diaminomethyl-bicyclo[2.2.1]heptane,
    (2S,6R)-diaminomethyl-bicyclo[2.2.1]heptane, and
    (2S,6S)-diaminomethyl-bicyclo[2.2.1]heptane.
(2S,5S)-NBDA:
    (2S,5S)-diaminomethyl-bicyclo[2.2.1]heptane.
(2S,5R)-NBDA:
    (2S,5R)-diaminomethyl-bicyclo[2.2.1]heptane.
(2S,6R)-NBDA:
    (2S,6R)-diaminomethyl-bicyclo[2.2.1]heptane.
(2S,6S)-NBDA:
    (2S,6S)-diaminomethyl-bicyclo[2.2.1]heptane.

The blend ratio of the starting compound isomers is as follows:
    (2S,5S)-NBDA:(2S,5R)-NBDA:(2S,6R)-NBDA:(2S,6S)-NBDA=26%:37%:18%:19%.

ii) Tetracarboxylic Dianhydride:
    PMDA: pyromellitic dianhydride.
    BPDA: 3,3',4,4'-biphenyltetracarboxylic dianhydride.
    BDTA: 3,3',4,4'-benzophenonetetracarboxylic dianhydride.
    ODPA: bis(3,4-dicarboxyphenyl) ether dianhydride.
    6FDA: 2,2-bis(3,4-dicarboxyphenyl)-1,1,1,3,3,3-hexafluoropropan dianhydride.

iii) Dicarboxylic Anhydride:
    PA: phthalic anhydride.

iv) Solvent:
    NMP: N-methyl-2-pyrrolidone.
    DMAc: N,N-dimethylacetamide.
    Cresol: mixture of p-cresol and m-cresol.

Production Examples

The NBDA isomer mixture for use in the present invention is prepared, for example, according to the Production Examples mentioned below. Combining these Production Examples gives various diamine isomer mixtures having different NBDA isomer composition ratios.

Production Example 1

A starting isomer mixture of NBDA was fed into a cylindrical column of glass having an inner diameter of 25 mm and a height of 200 mm, covered with a jacket and equipped with a switch cock at its bottom, and a small amount of seed crystal was added thereto and cooled to −15° C. In that condition, the system was completely solidified. Then, the switch cock at the bottom of the column was turned on, and the system was heated at a heating rate of 5° C./hr. The liquid phase was recovered in 7 fractions in all. Precisely, the fraction at −15° C. to lower than 6° C. is fraction 1; that at 6° C. is fraction 2; that at 6 to 12° C. is fraction 3; that at 12 to 17° C. is fraction 4; that at 17 to lower than 20° C. is fraction 5; that at 20° C. is fraction 6; and that at 20 to 25° C. is fraction 7. Each fraction was analyzed through liquid chromatography to determine the isomer composition ratio therein. The isomer composition of up to 50% of all the distillate was (2S,5S)-NBDA 30%, (2S,5R)-NBDA 42%, (2S,6R)-NBDA 13%, and (2S,6S)-NBDA 15%. In the final fraction 7, (2S,5S)-NBDA was 15%, (2S,5R)-NBDA was 22%, (2S,6R)-NBDA was 35%, and (2S,6S)-NBDA was 28%.

Each NBDA isomer was analyzed through high-performance liquid chromatography, for which the condition was as follows:

Device used: Nippon Bunko's high-performance liquid chromatography device (PU-980/UV-970).
Columns: YMC A-312 (ODS), 6φ×150 mm, 3 columns.
Column temperature: 50° C.
Transfer phase: acetonitrile/(50.01 mol/liter)-$KH_2PO_4$/$H_3PO_4$=1400/1800/5 (pH=2).
Flow rate: 0.8 ml/min.
Wavelength for detection: 254 nm.

Production Example 2

536.7 g of a starting isomer mixture of NBDA was fed into a cylindrical column of glass having an inner diameter of 48 mm and a height of 300 mm, covered with a jacket and equipped with a switch cock at its bottom, and cooled from room temperature to 10° C. over a period of 1 hour. Seed crystal was added thereto, and this was further cooled to −5° C. over a period of 3 hours. Then, this was kept cooled at −5° C. overnight, and NBDA was completely solidified.

After the complete solidification of NBDA was confirmed, the switch cock at the bottom of the column was turned on, and the system was gradually heated at a heating rate of 5° C./hr, and the liquid phase was recovered. In the same manner as in Production Example 1, the liquid phase was recovered in 12 fractions in all.

The isomer composition of up to 41% of all the distillate was (2S,5S)-NBDA 34%, (2S,5R)-NBDA 47%, (2S,6R)-NBDA 9%, and (2S,6S)-NBDA 10%. In the final fraction 12, (2S,5S)-NBDA was 5%, (2S,5R)-NBDA was 7%, (2S,6R)-NBDA was 45%, and (2S,6S)-NBDA was 43%.

Production Example 3

427.7 g of an isomer mixture of NBDA ((2S,5S)-NBDA 14%, (2S,5R)-NBDA 20%, (2S,6R)-NBDA 34%, (2S,6S)-NBDA 32%) was fed into the same device as that used in Production Example 2, and cooled to 5° C. to thereby completely solidify the entire system. Next, this was suitably heated from 15° C. up to 40° C., and the liquid phase was recovered in 6 fractions. In the final fraction 6, (2S,5S)-NBDA was 6%, (2S,5R)-NBDA was 8%, (2S,6R)-NBDA was 48%, and(2S,6S)-NBDA was 38%.

Production Example 4

115.0 g of an isomer mixture of NBDA ((2S,5S)-NBDA 5%, (2S,5R)-NBDA 7%, (2S,6R)-NBDA 44%, (2S,6S)-NBDA 44%) was fed into the same device as that used in Production Example 2, and cooled to 5° C. to thereby completely solidify the entire system. Next, this was suitably heated up to 30 to 40° C., and the liquid phase was fractionated. The amount of the final residual solid recovered was 53.7 g.

The isomer composition of the residual solid was (2S,5S)-NBDA 2%, (2S,5R)-NBDA 4%, (2S,6R)-NBDA 54%, and (2S,6S)-NBDA 40%.

Production Example 5

66.0 g of the NBDA mixture of (2S,5S)-NBDA 2%, (2S,5R)-NBDA 4%, (2S,6R)-NBDA 54% and (2S,6S)-NBDA 40% was mixed with 88.3 g of the NBDA mixture of (2S,5S)-NBDA 6%, (2S,5R)-NBDA 8%, (2S,6R)-NBDA 48% and (2S,6S)-NBDA 38% to obtain 154.3 g of an NBDA mixture of (2S,5S)-NBDA 21%, (2S,5R)-NBDA 29%, (2S,6R)-NBDA 28% and (2S,6S)-NBDA 22%.

Production Example 6

The NBDA isomer mixture obtained in Production Example 2, which has an isomer composition ratio of (2S,5S)-NBDA 34%, (2S,5R)-NBDA 47%, (2S,6R)-NBDA 9% and (2S,6S)-NBDA 10%, was passed through an optical resolution column to obtain an NBDA isomer mixture having an isomer composition ratio of (2S,5S)-NBDA 92%, (2S,5R)-NBDA 5%, (2S,6R)-NBDA 2% and (2S,6S)-NBDA 1%, and an NBDA isomer mixture having an isomer composition ratio of (2S,5S)-NBDA 3%, (2S,5R)-NBDA 94%, (2S,6R)-NBDA 2% and (2S,6S)-NBDA 1%.

Production Example 7

The NBDA isomer mixture obtained in Production Example 4, which has an isomer composition ratio of (2S,5S)-NBDA 2%, (2S,5R)-NBDA 4%, (2S,6R)-NBDA 54% and (2S,6S)-NBDA 40%, was passed through an optical resolution column to obtain an NBDA isomer mixture having an isomer composition ratio of (2S,5S)-NBDA 0%, (2S,5R)-NBDA 1%, (2S,6R)-NBDA 97% and (2S,6S)-NBDA 2%, and an NBDA isomer mixture having an isomer composition ratio of (2S,5S)-NBDA 1%, (2S,5R)-NBDA 1%, (2S,6R)-NBDA 2% and (2S,6S)-NBDA 96%.

Example 1

32.55 g (0.14925 mols) of PMDA and 90 g of NMP were fed into a flask equipped with a stirrer, a thermometer and a nitrogen-introducing duct, and stirred in a nitrogen atmosphere at room temperature. A mixed solution of 23.14 g (0.15 mols) of a diamine mixture, NBDA isomer mixture prepared in Production Example 2 ((2S,5S)-NBDA 34%, (2S,5R)-NBDA 47%, (2S,6R)-NBDA 9% and (2S,6S)-NBDA 10%) and 39.94 g of NMP was gradually and dropwise added to it over a period of 90 minutes. Then, this was heated up to 60° C., and further stirred for 6 hours. After cooled, this gave a polyamic acid, of which the inherent viscosity was 0.57 dl/g and the E-type machine viscosity was 24000 mPa·s.

The resulting varnish was cast on a glass sheet, heated in a nitrogen atmosphere from room temperature up to 250° C. for 2 hours, and baked at 250° C. for 2 hours to form a polyimide film having a thickness of about 50 μm. Regarding its appearance, the polyimide film was colorless and transparent, and flexible. As it was, however, the film greatly curled. The curl height R of the film was 20 mm. The yellowness index (YI) of the film was 4; the refractive index thereof was 1.58; and the birefringence thereof was 0.0185. The glass transition temperature (Tg) of the film was 302° C., and the 5% weight loss temperature (Td5) thereof was 421° C. Regarding its mechanical properties, the tensile strength (TS) of the film was 9.6 kgf/mm$^2$; the tensile modulus (TM) thereof was 181 kgf/mm$^2$; and the elongation (EL) was 9%. The dielectric constant of the film was 3.00; the volume resistivity thereof was $10^{16}$ Ω·cm; and the surface resistivity thereof was $10^{16}$Ω. These data are given in Table 1.

Example 2

A polyamic acid varnish was obtained in the same manner as in Example 1, for which, however, used was the NBDA isomer mixture prepared in Production Example 4 ((2S,5S)-NBDA 2%, (2S,5R)-NBDA 4%, (2S,6R)-NBDA 54% and (2S,6S)-NBDA 40%) in place of the NBDA isomer mixture used in Example 1. The polyamic acid obtained herein had a inherent viscosity of 0.34 dl/g; and its varnish had an E-type machine viscosity of 9250 mPa·s.

Further in the same manner as in Example 1, a polyimide film was obtained from the polyamic acid. It was cloudy but a little. The polyimide film was analyzed through wide-angle X-ray diffractiometry, and its pattern had small diffraction peaks. From this, it is believed that an extremely small part of the polyimide film would have crystallized. FIG. 1 shows the wide-angle X-ray diffraction patter of the film. The curl height R of the film was 0, and the film was almost flat. YI of the film was 4; the refractive index thereof was 1.52; and the birefringence thereof was 0.0122. Tg of the film was 270° C.; Td5 thereof was 434° C.; TS thereof was 5.1 kgf/mm$^2$; TM thereof was 211 kgf/mm$^2$; and EL thereof was 4%. The dielectric constant of the film was 3.1; the volume resistivity thereof was $10^{16}$ Ω·cm; and the surface resistivity thereof was $10^{16}$Ω. These data are given in Table 1.

Example 3

A polyamic acid varnish was obtained in the same manner as in Example 1, for which, however, used was the NBDA isomer mixture prepared in Production Example 5 ((2S,5S)-NBDA 21%, (2S,5R)-NBDA 29%, (2S,6R)-NBDA 28% and (2S,6S)-NBDA 22%) in place of the NBDA isomer mixture used in Example 1. The polyamic acid obtained herein had a inherent viscosity of 0.42 dl/g; and its varnish had an E-type machine viscosity of 24550 mPa·s. Further in the same manner as in Example 1, a polyimide film was obtained from the polyamic acid. Its curl height R was 0, and the film was almost smooth, neither curled nor warped. YI of the film was 6; the refractive index thereof was 1.55; and the birefringence thereof was 0.0146. Tg of the film was 282° C.; Td5 thereof was 436° C.; TS thereof was 9.1 kgf/mm$^2$; TM thereof was 160 kgf/mm$^2$; and EL thereof was 8%. The dielectric constant of the film was 2.9; the volume resistivity thereof was $10^{16}$ Ω·cm; and the surface resistivity thereof was $10^{16}$Ω. These data are given in Table 1.

Example 4

A polyamic acid varnish was obtained in the same manner as in Example 1, for which, however, used was the starting NBDA isomer mixture (composed of (2S,5S)-NBDA 26%, (2S,5R)-NBDA 37%, (2S,6R)-NBDA 18% and (2S,6S)-NBDA 19%) in place of the NBDA isomer mixture used in Example 1. The polyamic acid obtained herein had a inherent viscosity of 0.51 dl/g; and its varnish had an E-type machine viscosity of 29850 mPa·s. Further in the same manner as in Example 1, a polyimide film was obtained from the polyamic acid. It was almost smooth, but its curl height R was 4 mm. The film curled and warped but a little. YI of the film was 6; the refractive index thereof was 1.56; and the birefringence thereof was 0.0144. Tg of the film was 291° C.; Td5 thereof was 426° C.; TS thereof was 9.5 kgf/mm$^2$; TM thereof was 170 kgf/mm$^2$; and EL thereof was 7%. The dielectric constant of the film was 3.0; the volume resistivity thereof was $10^{16}$ Ω·cm; and the surface resistivity thereof was $10^{16}$Ω. These data are given in Table 1.

Example 5

A polyamic acid varnish was obtained in the same manner as in Example 1, for which, however, used was an NBDA isomer mixture (composed of (2S,5S)-NBDA 18%, (2S,5R)-NBDA 19%, (2S,6R)-NBDA 26% and (2S,6S)-NBDA 37%) in place of the NBDA isomer mixture used in Example 1. The polyamic acid obtained herein had a inherent viscosity of 0.55 dl/g; and its varnish had an E-type machine viscosity of 30020 mPa·s. Further in the same manner as in Example 1, a polyimide film was obtained from the polyamic acid. It was almost smooth, but its curl height R was 5 mm. The film curled and warped but a little. YI of the film was 5; the refractive index thereof was 1.56; and the birefringence thereof was 0.0145. Tg of the film was 292° C.; Td5 thereof was 426° C.; TS thereof was 9.7 kgf/mm$^2$; TM thereof was 168 kgf/mm$^2$; and EL thereof was 7%. The dielectric constant of the film was 3.0; the volume resistivity thereof was $10^{16}$ Ω·cm; and the surface resistivity thereof was $10^{16}$Ω. These data are given in Table 1.

Comparative Example 1

A polyamic acid varnish was obtained in the same manner as in Example 1, for which, however, used was the NBDA isomer mixture prepared in Production Example 6 ((2S,5S)-NBDA 92%, (2S,5R)-NBDA 5%, (2S,6R)-NBDA 2% and (2S,6S)-NBDA 1%) in place of the NBDA isomer mixture used in Example 1. The polyamic acid obtained herein had a inherent viscosity of 0.50 dl/g; and its varnish had an E-type machine viscosity of 28750 mPa·s. Like in Example 1, the polyamic acid varnish obtained herein was cast on a glass sheet, and baked in a nitrogen atmosphere at 250° C. for 2 hours. However, it was partly whitened and crystallized, and was extremely brittle, and it could not form a polyimide film. These data are given in Table 1.

Comparative Example 2

A polyamic acid varnish was obtained in the same manner as in Example 1, for which, however, used was the NBDA isomer mixture prepared in Production Example 6 ((2S,5S)-NBDA 3%, (2S,5R)-NBDA 94%, (2S,6R)-NBDA 2% and (2S,6S)-NBDA 1%) in place of the NBDA isomer mixture used in Example 1. The polyamic acid obtained herein had a inherent viscosity of 0.21 dl/g; and its varnish had an E-type machine viscosity of 7730 mPa·s. Like in Example 1, the polyamic acid varnish obtained herein was cast on a glass sheet, and baked in a nitrogen atmosphere at 250° C. for 2 hours. However, it was extremely brittle, and could not form a polyimide film. These data are given in Table 1.

Comparative Example 3

A polyamic acid varnish was obtained in the same manner as in Example 1, for which, however, used was the NBDA isomer mixture prepared in Production Example 7 ((2S,5S)-NBDA 0%, (2S,5R)-NBDA 1%, (2S,6R)-NBDA 97% and (2S,6S)-NBDA 2%) in place of the NBDA isomer mixture used in Example 1. The polyamic acid obtained herein had a inherent viscosity of 0.44 dl/g; and its varnish had an E-type machine viscosity of 15850 mPa·s. Like in Example 1, the polyamic acid varnish obtained herein was cast on a glass sheet, and baked in a nitrogen atmosphere at 250° C.

for 2 hours. However, it was partly whitened and crystallized, and was extremely brittle, and it could not form a polyimide film. These data are given in Table 1.

Comparative Example 4

Figure 2:
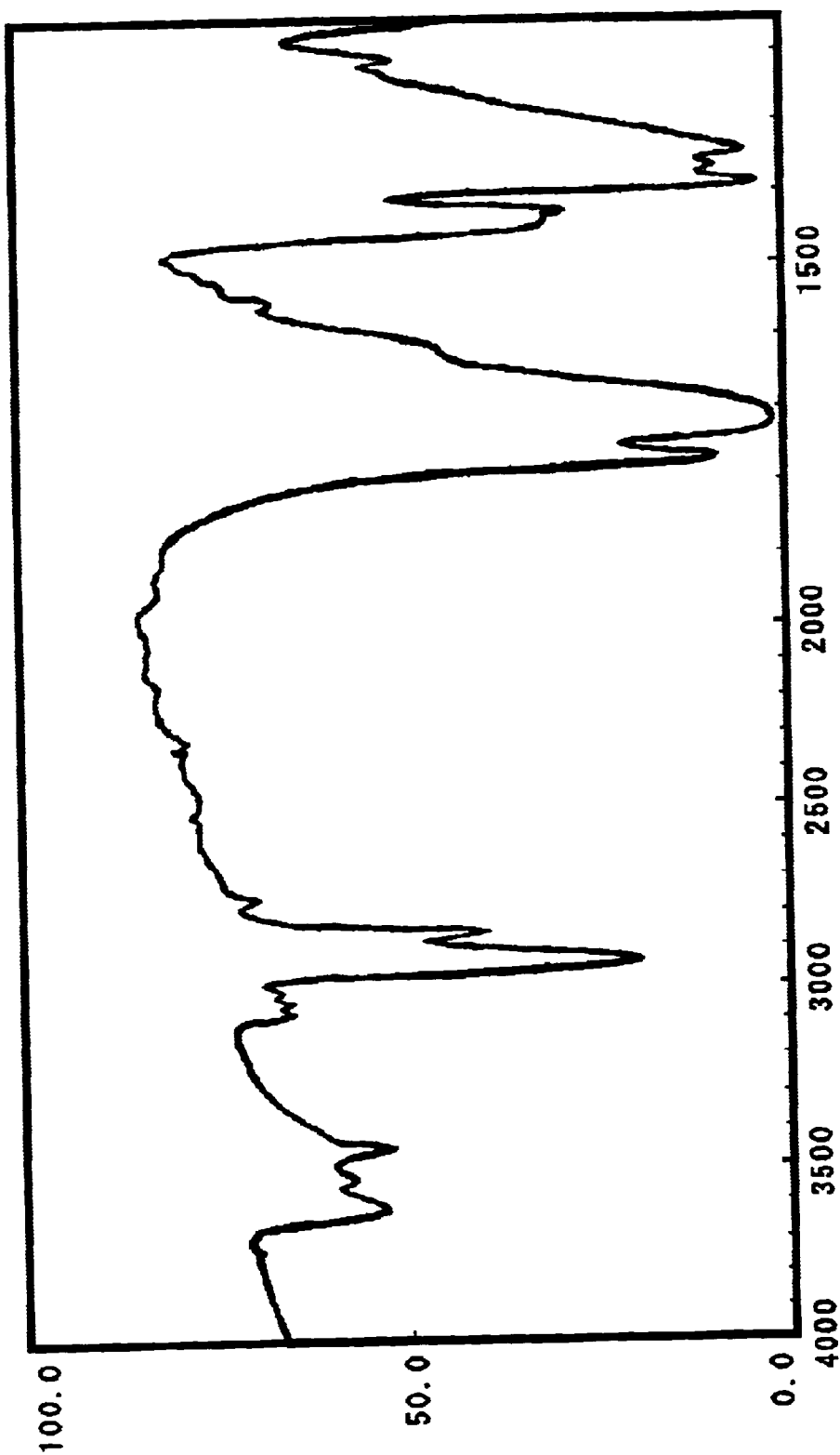
FIG. 2 shows an IR spectral pattern of the polyimide obtained in Example 6.

A polyamic acid varnish was obtained in the same manner as in Example 1, for which, however, used was the NBDA isomer mixture prepared in Production Example 7 ((2S,5S)-NBDA 1%, (2S,5R)-NBDA 1%, (2S,6R)-NBDA 2% and (2S,6S)-NBDA 96%) in place of the NBDA isomer mixture used in Example 1. The polyamic acid obtained herein had a inherent viscosity of 0.18 dl/g; and its varnish had an E-type machine viscosity of 5130 mPa·s. Like in Example 1, the polyamic acid varnish obtained herein was cast on a glass sheet, and baked in a nitrogen atmosphere at 250° C. for 2 hours. However, it was extremely brittle, and could not form a polyimide film. These data are given in Table 1.

imide deposit was recovered through filtration, fully washed with about 1 liter of methanol, and dried in a nitrogen atmosphere at 120° C. for 8 hours and at 230° C. for 4 hours to obtain 33.3 g (yield: 99.2%) of a polyimide powder. The thus-obtained polyimide powder was pale grayish white, and its inherent viscosity was 0.85 dl/g. The IR spectrometry of the powder obtained herein showed absorption at around 1780 $cm^{-1}$ and around 1720 $cm^{-1}$ derived from imide bonds, which confirmed that the powder is a polyimide. It further showed absorption of the stretching vibration of methylene chains derived from an alicyclic compound at around 2800 to 3200 $cm^{-1}$, which confirmed that the compound has an NBDA skeleton introduced thereinto. FIG. 2 shows the IR spectral chart of the compound. The polyimide powder obtained herein had Tg of 285° C. and Td5 of 374° C. The melt flow point of the polyimide powder was 335° C., and the melt viscosity thereof at 380° C. was 3250 Pa·s. The polyimide powder was quite insoluble in 1,1,2,2-tetrachloroethane.

TABLE 1

| Example | NBDA isomer composition rate (%) (2S,5S):(2S,5R):(2S,6R):(2S,6S) | Acid dianhydride | η inh *1 (dl/g) | E type mechanical viscosity (mPa · s) | YI *2 | Refractive index | Birefringence | Tg *3 (° C.) | Td5 *4 (° C.) |
|---|---|---|---|---|---|---|---|---|---|
| 1 | 34:47:9:10 | PMDA | 0.57 | 24000 | 4 | 1.58 | 0.0186 | 302 | 421 |
| 2 | 2:4:54:40 | ↑ | 0.34 | 9250 | 4 | 1.52 | 0.0122 | 270 | 434 |
| 3 | 21:29:28:22 | ↑ | 0.42 | 24550 | 6 | 1.55 | 0.0146 | 282 | 436 |
| 4 | 26:37:18:19 | ↑ | 0.51 | 29850 | 6 | 1.56 | 0.0144 | 291 | 426 |
| 5 | 18:19:26:37 | ↑ | 0.55 | 30020 | 5 | 1.56 | 0.0145 | 292 | 426 |
| Comparative example | | | | | | | | | |
| 1 | 92:5:2:1 | PMDA | 0.50 | 28750 | Not measured for impossible to form film | | | | |
| 2 | 3:94:2:1 | ↑ | 0.21 | 7730 | ↑ | | | | |
| 3 | 0:1:97:2 | ↑ | 0.44 | 15850 | ↑ | | | | |
| 4 | 1:1:2:94 | ↑ | 0.18 | 5130 | ↑ | | | | |

| Example | TS *5 (kgf/mm²) | TM *6 (kgf/mm²) | EL *7 (%) | Dielectric constant | Volume resistivity (Ω · cm) | Surface resistivity (Ω) | Curl height R *8 (mm) |
|---|---|---|---|---|---|---|---|
| 1 | 9.6 | 181 | 9 | 3.0 | $10^{16}$ | $10^{16}$ | 20 |
| 2 | 5.1 | 211 | 4 | 3.1 | $10^{16}$ | $10^{16}$ | 0 |
| 3 | 9.1 | 160 | 8 | 2.9 | $10^{16}$ | $10^{16}$ | 0 |
| 4 | 9.5 | 170 | 7 | 3.0 | $10^{16}$ | $10^{16}$ | 4 |
| 5 | 9.7 | 168 | 7 | 3.0 | $10^{16}$ | $10^{16}$ | 5 |
| Comparative example | | | | | | | |
| 1~4 | Not measured for impossible to form film | | | | | | |

*1 Inherent viscosity of polyamic acid
*2 Yellowness Index
*3 Glass transition temperature
*4 5% weight loss temperature
*5 Tensile strength
*6 Tensile modulus
*7 Elongation
*8 Curl height (curvature length)

Example 6

15.43 g (0.1 mols) of the NBDA isomer mixture prepared in Production Example 2 ((2S,5S)-NBDA 34%, (2S,5R)-NBDA 47%, (2S,6R)-NBDA 9% and (2S,6S)-NBDA 10%), 21.59 g (0.099 mols) of PMDA, 0.15 g (0.01 mols) of PA and 148.96 g of cresol were fed into a flask equipped with a stirrer, a thermometer, a nitrogen-introducing duct and a condenser. The reaction system was heated from room temperature up to 200° C. over a period of about 2 hours, and then reacted at 200° C. for 4 hours. After thus reacted, the reaction system was left to be at room temperature, and poured into 500 ml of methanol with stirring at high speed to deposit a powdery polyimide therein. The powdery poly- Examples 7 to 9

Polyimide powders were obtained in the same manner as in Example 6, for which, however, the dianhydrides shown in Table 2 were used. The yield, the inherent viscosity, Tg, Td5, the melt flow point and the melt viscosity of the polyimide powders are shown in Table 2, along with the data of the polyimide powder of Example 6.

Examples 10 to 15

Polyimide powders were obtained in the same manner as in Example 6, for which, however, the NBDA isomer mixture prepared in Production Example 3 ((2S,5S)-NBDA 6%, (2S,5R)-NBDA 8%, (2S,6R)-NBDA 48% and (2S,6S)-NBDA 38%) was used in place of the NBDA isomer mixture used in Example 6 and the dianhydrides shown in Table 2 were used. The polyimide powder of Example 11 was quite insoluble in 1,1,2,2-tetrachloroethane. The yield, the inherent viscosity, Tg, Td5, the melt flow point and the melt viscosity of the polyimide powders are shown in Table 2.

Examples 16 to 20

Polyimide powders were obtained in the same manner as in Example 6, for which, however, the NBDA isomer mixture prepared in Production Example 5 ((2S,5S)-NBDA 21%, (2S,5R)-NBDA 29%, (2S,6R)-NBDA 28% and (2S,6S)-NBDA 22%) was used in place of the NBDA isomer mixture used in Example 4 and the dianhydrides shown in Table 2 were used. The polyimide powder of Example 16 was soluble in 1,1,2,2-tetrachloroethane, and its solubility therein was 20% by weight. The yield, the inherent viscosity, Tg, Td5, the melt flow point and the melt viscosity of the polyimide powders are shown in Table 2.

TABLE 2

| Example | Acid dianhydride | NBDA isomer composition rate (%) (2S,5S):(2S,5R) (2S,6R):(2S,6S) | Yield (%) | η inh *1 (dl/g) | Tg *2 (° C.) | Td5 *3 (° C.) | Initial melt flow temperature (° C.) | Melt viscosity *4 (Pa · s) |
|---|---|---|---|---|---|---|---|---|
| 6 | PMDA | 34:47:9:10 | 99.2 | 0.85 | 285 | 374 | 335 | 3250 (380° C.) |
| 7 | BPDA | ↑ | 96.7 | 0.99 | 254 | 421 | 330 | 1576 (370° C.) |
| 8 | ODPA | ↑ | 98.1 | 0.58 | 214 | 443 | 275 | 1673 (330° C) |
| 9 | BTDA | ↑ | 97.2 | 0.31 | 218 | 445 | 275 | 982 (330° C.) |
| 10 | 6FDA | ↑ | 96.1 | 0.44 | 241 | 414 | 315 | 2814 (370° C.) |
| 11 | PMDA | 6:8:78:38 | 88.4 | 0.23 | 255 | 427 | 315 | 345 (360° C.) |
| 12 | BPDA | ↑ | 97.0 | 0.45 | 234 | 445 | 310 | 2019 (350° C.) |
| 13 | ODPA | ↑ | 97.8 | 0.50 | 205 | 456 | 270 | 2293 (320° C.) |
| 14 | BTDA | ↑ | 100.0 | 0.47 | 218 | 441 | 280 | 3422 (330° C.) |
| 15 | 6FDA | ↑ | 93.9 | 0.44 | 232 | 441 | 310 | 4211 (330° C.) |
| 16 | PMDA | 21:29:28:22 | 96.5 | 0.43 | 276 | | 416 | 445 (370° C.) |
| 17 | BPDA | ↑ | 97.5 | 0.66 | 241 | 445 | 325 | 1285 (370° C.) |
| 18 | ODPA | ↑ | 98.6 | 0.50 | 210 | 450 | 280 | 1131 (330° C.) |
| 19 | BTDA | ↑ | 98.8 | 0.38 | 219 | 450 | 285 | 2275 (330° C.) |
| 20 | 6FDA | ↑ | 96.7 | 0.51 | 239 | 407 | 315 | 4497 (330° C.) |

*1 Inherent viscosity of polyimide powder
*2 Glass transition temperature
*3 5% weight loss temperature
*4 Measuring temperature in parenthesis Industrial Applicability As in the present invention, the inventors have found that polyimide films or polyimide powders can be obtained by varying the isomer composition ratio of the four structural isomers of an alicyclic diamine, diaminomethyl-bicyclo[2.2.1]heptane (NBDA), or that is, (2S,5S)-NBDA, (2S,5R)-NBDA, (2S,6R)-NBDA and (2S,6S)-NBDA, and that the properties, such as the thermal resistance (Tg), the optical properties (refractive index, birefringence), the melt flowability (melt flow point) and the solubility in solvents of the polyamic acids and the polyimides obtained, and also the crystallinity and the curling and warping properties of the polyimide films can be controlled.

What is claimed is:

1. A polyamic acid having repeating units represented by the formula (1):

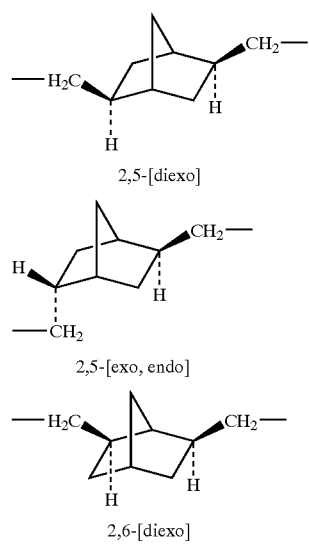

(1)

wherein the norbornane skeleton of comprises four components of 2,5-[diexo]

2,5-[exo, endo]

2,6-[diexo]

-continued

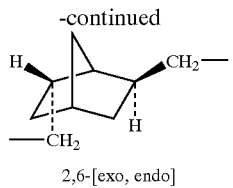
2,6-[exo, endo]

and their contents satisfy the following:

1% ≦ 2,5-[diexo] ≦ 90%,
1% ≦ 2,5-[exo,endo] ≦ 90%,
1% ≦ 2,6-[diexo] ≦ 90%,
1% ≦ 2,6-[exo,endo] ≦ 90%, provided that (2,5-[diexo])+(2,5-[exo,endo])+(2,6-[diexo])+(2,6-[exo,endo])= 100%.

R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member, wherein the polyamic acid has an inherent viscosity measured in a solvent of N-methyl-2-pyrrolidone having an acid concentration of 0.5 g/dl at 35° C. that falls between 0.1 and 3.0 dl/g.

2. A polyamic acid having repeating units represented by the formula (1):

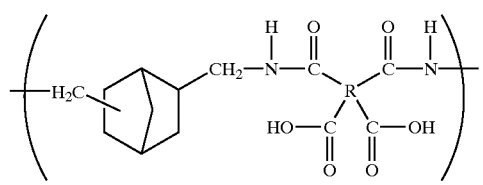 (1)

wherein the norbornane skeleton of

comprises four components of

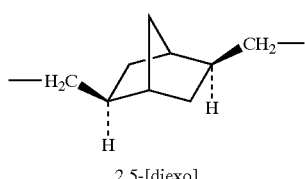
2,5-[diexo]

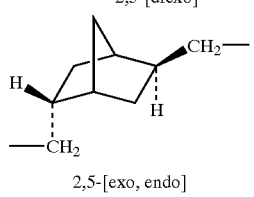
2,5-[exo, endo]

-continued

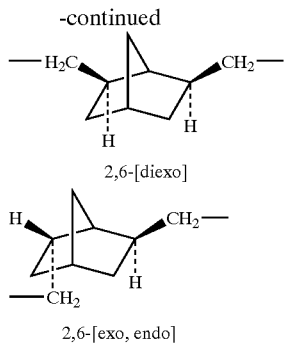
2,6-[diexo]

2,6-[exo, endo]

and their contents satisfy the following:

10% ≦ 2,5-[diexo] ≦ 40%,
10% ≦ 2,5-[exo,endo] ≦ 40%,
10% ≦ 2,6-[diexo] ≦ 40%,
10% ≦ 2,6-[exo,endo] ≦ 40%, provided that (2,5-[diexo])+(2,5-[exo,endo])+(2,6-[diexo])+(2,6-[exo,endo])= 100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member.

3. A polyamic acid having repeating units represented by the formula (1):

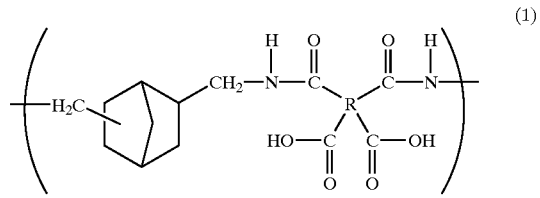 (1)

wherein the norbornane skeleton of

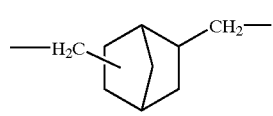

comprises four components of

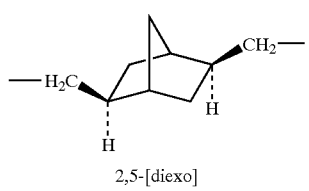
2,5-[diexo]

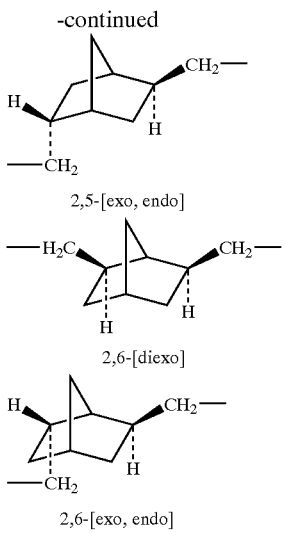

2,5-[exo, endo]

2,6-[diexo]

2,6-[exo, endo]

and their contents satisfy the following:

20% ≦ 2,5-[diexo] ≦ 30%,

20% ≦ 2,5-[exo,endo]30%,

20% 2,6-[diexo] ≦ 30%,

20% ≦ 2,6-[exo,endo]+30%, provided that (2,5-[diexo])+(2,5-[exo,endo])+(2,6-[diexo])+(2,6-[exo,endo])= 100%, R represents a tetravalent group having from 4 to 27 carbon atoms, and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member.

4. A polyimide having repeating units represented by the formula (2):

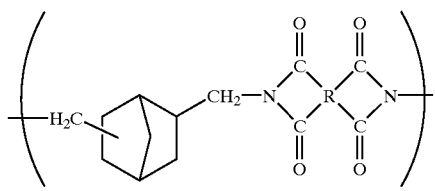 (2)

wherein the norbornane skeleton of

comprises four components of

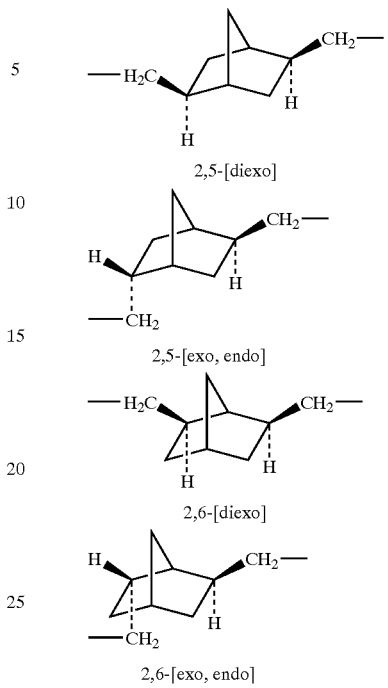

2,5-[diexo]

2,5-[exo, endo]

2,6-[diexo]

2,6-[exo, endo]

and their contents satisfy the following:

1% ≦ 2,5-[diexo] ≦ 90%,

1% ≦ 2,5-[exo,endo] ≦ 90%,

1% ≦ 2,6-[diexo] ≦ 90%,

1% ≦ 2,6-[exo,endo] ≦ 90%, provided that (2,5-[diexo])+(2,5-[exo,endo])+(2,6-[diexo])+(2,6-[exo,endo])= 100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member, wherein the polyimide has an inherent viscosity measured in a mixed solvent of p-chlorophenyl/phenol=9/1 (by weight) with a polyimide concentration of 0.5 g/dl at 35° C. that falls between 0.1 and 3.0 dl/g.

5. A polyimide having repeating units represented by the formula (2):

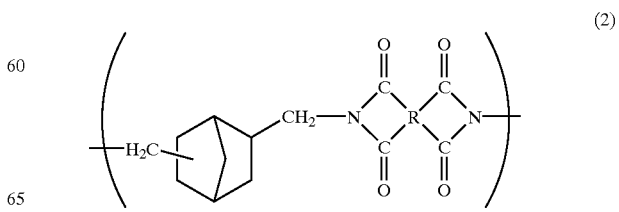 (2)

wherein the norbornane skeleton of

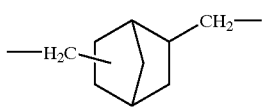

comprises four components of

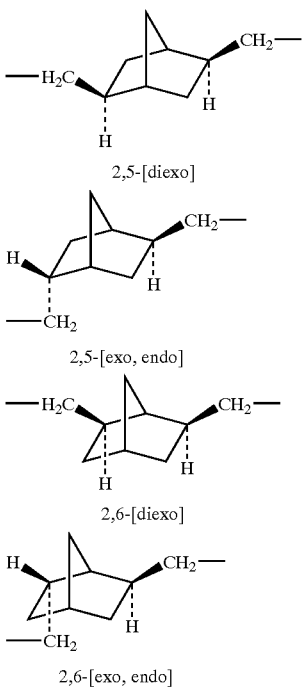

2,5-[diexo]

2,5-[exo, endo]

2,6-[diexo]

2,6-[exo, endo]

and their contents satisfy the following:

$10\% \leq 2,5\text{-[diexo]} \leq 40\%$, $10\% \leq 2,5\text{-[exo,endo]} \leq 40\%$, $10\% \leq 2,6\text{-[diexo]} \leq 40\%$, $10\% \leq 2,6\text{-[exo,endo]} \leq 40\%$, provided that (2,5-[diexo])+(2,5-[exo,endo])+(2,6-[diexo])+(2,6-[exo,endo])= 100%, R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member.

6. A polyimide having repeating units represented by the formula (2):

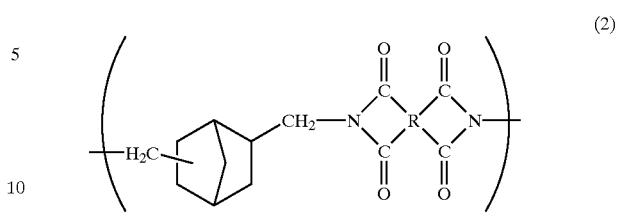

(2)

wherein the norbornane skeleton of

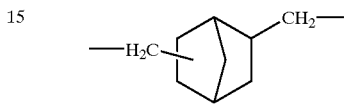

comprises four components of

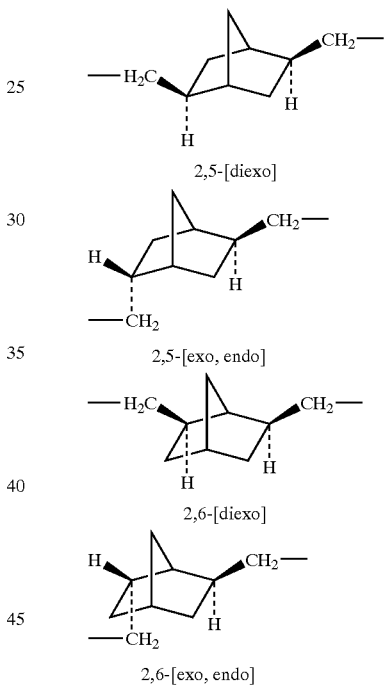

2,5-[diexo]

2,5-[exo, endo]

2,6-[diexo]

2,6-[exo, endo]

and their contents satisfy the following:
$20\% \leq 2,5\text{-[diexo]} \leq 30\%$,
$20\% \leq 2,5\text{-[exo,endo]} \leq 30\%$,
$20\% \leq 2,6\text{-[diexo]} \leq 30\%$,
$20\% \leq 2,6\text{-[exo,endo]} \leq 30\%$,
provided that (2,5-[diexo])+(2,5-[exo,endo])+(2,6-[diexo])+(2,6-[exo,endo])= 100%, R represents a tetravalent group having from 4 to 27 carbon atoms, and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member.

7. A process for preparing a polyamic acid, which comprises reacting a mixture of diaminomethyl-bicyclo[2.2.1]

heptanes, (2S,5S)-diaminomethyl-bicyclo[2.2.1]heptane of formula (3-1):

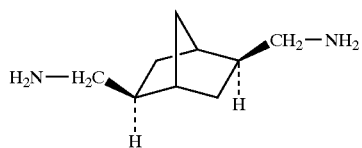
(3-1)

(2S,5R)-diaminomethyl-bicyclo[2.2.1]heptane of formula (3-2):

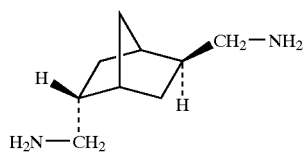
(3-2)

(2S6R)-diaminomethyl-bicyclo[2.2.1]heptane of formula (3-3):

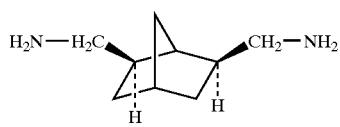
(3-3)

and (2S,6S)-diaminomethyl-bicyclo[2.2.1]heptane of formula (3-4):

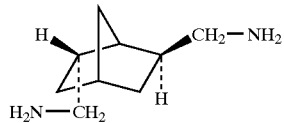
(3-4)

wherein,

10% ≦ (2S,5S)-diaminomethyl-bicyclo[2.2.1]heptane ≦ 40%,

10% ≦ (2S,5R)-diaminomethyl-bicyclo[2.2.1]heptane ≦ 40%,

10% ≦ (2S,6R)-diaminomethyl-bicyclo[2.2.1]heptane ≦ 40%,

10% ≦ (2S,6S)-diaminomethyl-bicyclo[2.2.1]heptane ≦ 4.0%, provided that, (2S,5S)isomer+(2S,5R)isomer+(2S,6R)isomer+(2S,6S) isomer= 100%, with a tetracarboxylic dianhydride represented by the formula (4):

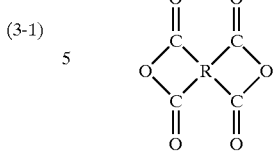
(4)

wherein R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member.

8. A process for preparing a polyamic acid, which comprises reacting a mixture of diaminomethyl-bicyclo[2.2.1] heptanes, (2S,5S)-diaminomethyl-bicyclo[2.2.1]heptane of formula (3-1):

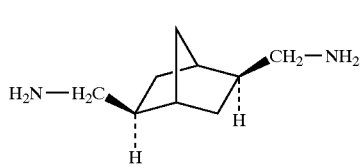
(3-1)

(2S,5R)-diaminomethyl-bicyclo[2.2.1]heptane of formula (3-2):

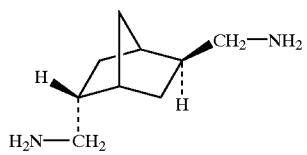
(3-2)

(2S,6R)-diaminomethyl-bicyclo[2.2.1]heptane of formula (3-3):

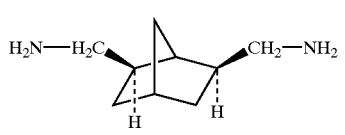
(3-3)

and (2S,6S)-diaminomethyl-bicyclo[2.2.1]heptane of formula (3-4):

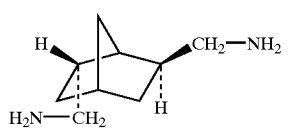
(3-4)

wherein,

20% ≦ (2S,5S)-diaminomethyl-bicyclo[2.2.1]heptane ≦ 30%,

20% ≦ (2S,5R)-diaminomethyl-bicyclo[2.2.1]heptane ≦ 30%,

20% ≦ (2S6R)-diaminomethyl-bicyclo[2.2.1]heptane ≦ 30%,

20%≦(2S6S)-diaminomethyl-bicyclo[2.2.1]heptane≦30%,
provided that, (2S,5S)isomer+(2S,5R)isomer+(2S,6R)isomer+(2S,6S)isomer= 100%, with a tetracarboxylic dianhydride represented by the formula (4):

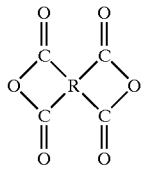

(4)

wherein R represents a tetravalent group having from 4 to 27 carbon atoms and selected from the group consisting of an aliphatic group, a monocyclic aliphatic group, a condensed polycyclic aliphatic group, a monocyclic aromatic group, a condensed polycyclic aromatic group, and a non-condensed polycyclic aliphatic or aromatic group which is composed of cycloaliphatic or aromatic groups mutually bonded to each other either directly or via a crosslinking member.

9. A process for preparing a polyimide, which comprises thermally or chemically imidizing the polyamic acid obtained in claim 7.

10. A process for preparing a polyimide, which comprises thermally or chemically imidizing the polyamic acid obtained in claim 8.

11. The polyamic acid of claim 3, of which the inherent viscosity measured in a solvent of N-methyl-2-pyrrolidone having the acid concentration of 0.5 g/dl at 35° C. falls between 0.1 and 3.0 dl/g.

12. The polyimide of claim 6, of which the inherent viscosity measured in a mixed solvent of p-chlorophenyl/phenol=9/1 (by weight) having the polyimide concentration of 0.5 g/dl at 35° C. falls between 0.1 and 3.0 dl/g.

13. A polyamic acid varnish containing the polyamic acid of claim 1.

14. A polyamic acid varnish containing the polyamic acid of claim 2.

15. A polyamic acid varnish containing the polyamic acid of claim 3.

16. A polyimide film containing the polyimide of claim 4.

17. An amorphous polyimide film containing the polyimide of claim 5.

18. An amorphous polyimide film of improved smoothness, containing the polyimide of claim 6.

19. The polyamic acid of claim 2, of which the inherent viscosity measured in a solvent of N-methyl-2-pyrrolidone having the acid concentration of 0.5 g/dl at 35° C. falls between 0.1 and 3.0 dl/g.

20. The polyimide of claim 5, of which the inherent viscosity measured in a mixed solvent of p-chlorophenyl/phenol=9/1 (by weight) having the polyimide concentration of 0.5 g/dl at 35° C. falls between 0.1 and 3.0 dl/g.

* * * * *